US010415382B2

(12) United States Patent
Enkababian et al.

(10) Patent No.: US 10,415,382 B2
(45) Date of Patent: Sep. 17, 2019

(54) METHOD AND SYSTEM FOR ESTABLISHING WELL PERFORMANCE DURING PLUG MILL-OUT OR CLEANOUT/WORKOVER OPERATIONS

(71) Applicant: Schlumberger Technology Corporation, Sugar Land, TX (US)

(72) Inventors: Philippe Enkababian, Richmond, TX (US); Dmitriy Potapenko, Sugar Land, TX (US); Dean Willberg, Salt Lake City, UT (US)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 304 days.

(21) Appl. No.: 15/145,396

(22) Filed: May 3, 2016

(65) Prior Publication Data

US 2017/0321547 A1 Nov. 9, 2017

(51) Int. Cl.
*E21B 49/08* (2006.01)
*E21B 29/00* (2006.01)
*E21B 33/134* (2006.01)
*E21B 43/26* (2006.01)
*E21B 47/06* (2012.01)
*E21B 47/10* (2012.01)
*E21B 49/00* (2006.01)
*G01N 15/08* (2006.01)
*G01V 9/00* (2006.01)

(52) U.S. Cl.
CPC ............ *E21B 49/086* (2013.01); *E21B 29/00* (2013.01); *E21B 29/002* (2013.01); *E21B 33/134* (2013.01); *E21B 43/26* (2013.01); *E21B 47/06* (2013.01); *E21B 47/1015* (2013.01); *E21B 49/00* (2013.01); *G01N 15/088* (2013.01); *G01V 9/00* (2013.01)

(58) Field of Classification Search
CPC .... E21B 49/086; E21B 20/002; E21B 33/134; E21B 47/1015; E21B 49/00; E21B 47/06; E21B 34/14; E21B 47/10; E21B 33/12; E21B 43/26; E21B 41/0092; E21B 2034/007; G06F 17/5009; G01F 1/74; G01N 15/088; G01V 9/00
See application file for complete search history.

(56) References Cited

U.S. PATENT DOCUMENTS 8,536,524 B2 9/2013 Pomerantz et al.
2006/0113077 A1 6/2006 Willberg et al.
(Continued)

OTHER PUBLICATIONS

International Search Report and Written Opinion issued in the related PCT Application PCT/US2017/030721, dated Jul. 11, 2017 (17 pages).

(Continued)

*Primary Examiner* — Yong-Suk Ro
(74) *Attorney, Agent, or Firm* — Cameron R. Sneddon

(57) ABSTRACT

A method and system is provided that analyzes flow characteristics of return fluid that flows to a surface-located facility during well operations (such as plug mill-out or cleanout/workover operations) in order to characterize local formation properties of the formation. The method and system can be used to characterize a hydraulically-fractured hydrocarbon-bearing formation that is traversed by a well having a number of intervals that are hydraulically isolated from one another by corresponding plugs.

37 Claims, 17 Drawing Sheets

(56) References Cited

U.S. PATENT DOCUMENTS

| | | |
|---|---|---|
| 2008/0093073 A1 | 4/2008 | Bustos et al. |
| 2008/0099241 A1 | 5/2008 | Ibrahim et al. |
| 2008/0133193 A1 | 6/2008 | Gdanski et al. |
| 2008/0173453 A1 | 7/2008 | Misselbrook |
| 2008/0210470 A1 | 9/2008 | Stewart |
| 2012/0125627 A1 | 5/2012 | George et al. |
| 2012/0181034 A1 | 7/2012 | Bour et al. |
| 2015/0034308 A1 | 2/2015 | Blair et al. |
| 2016/0024902 A1 | 1/2016 | Richter et al. |

OTHER PUBLICATIONS

K. Bendiksen et al, "The dynamic two-fluid model OLGA: theory and application," SPE Prod. Eng., 1991, pp. 171-180.

International Patent Application No. PCT/US2016/014424 filed Jan. 22, 2016; 83 pages.

International Preliminary Report on Patentability issued in the related PCT Application PCT/US2017/030721, dated Nov. 15, 2018 (8 pages).

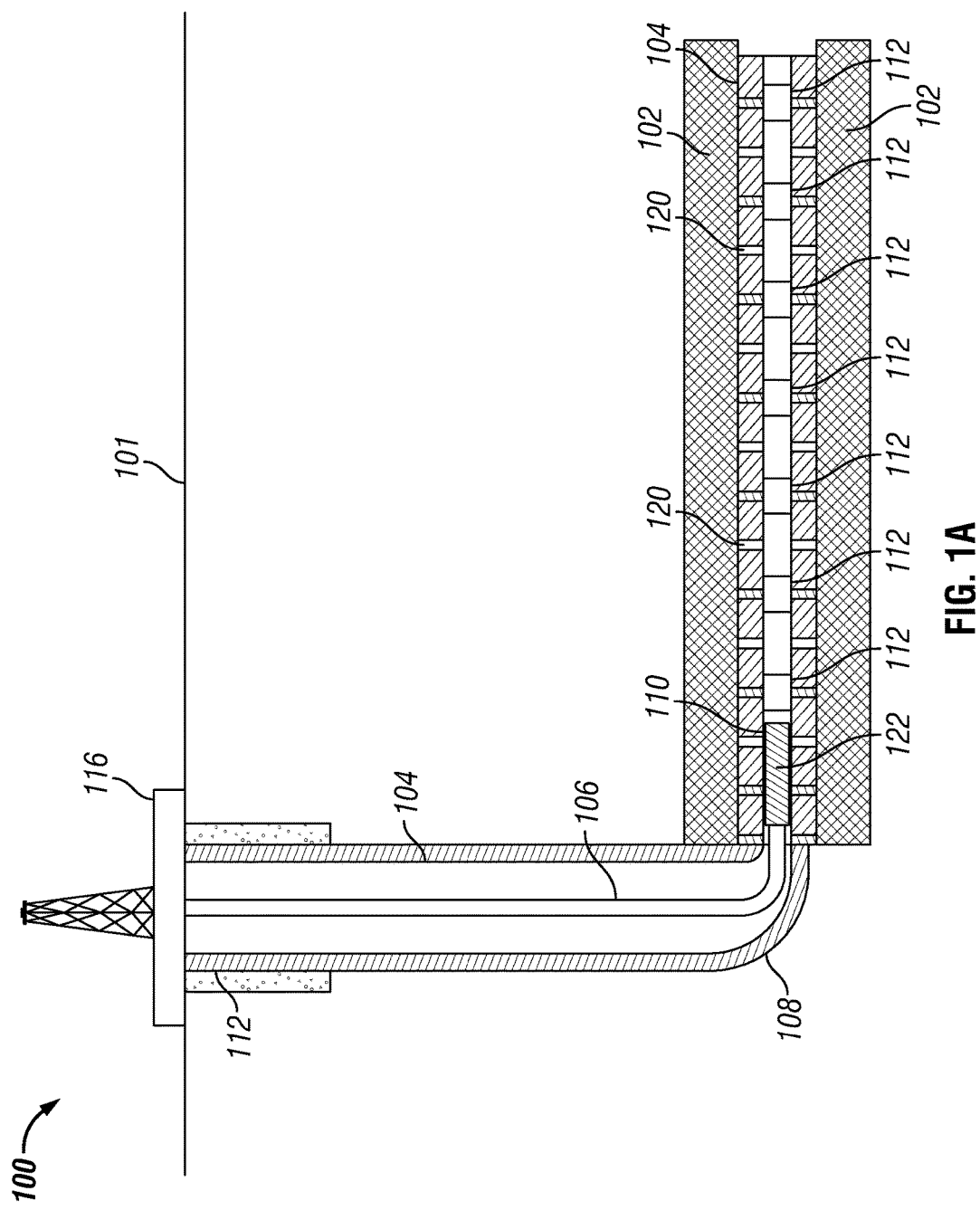

METHOD AND SYSTEM FOR ESTABLISHING WELL PERFORMANCE DURING PLUG MILL-OUT OR CLEANOUT/WORKOVER OPERATIONS

BACKGROUND

Exploring, drilling and completing hydrocarbon and other wells are generally complicated, time consuming and ultimately very expensive endeavors. In recognition of these expenses, added emphasis has been placed on efficiencies associated with well completions and maintenance over the life of the well. Over the years, ever increasing well depths and sophisticated architecture have made reductions in time and effort spent in completions and maintenance operations of even greater focus.

Perforating and fracturing applications in a well, which occurs generally during well completion, constitute one such area where significant amounts of time and effort are spent, particularly as increases in well depths and sophisticated architecture are encountered. These applications can involve the positioning of a bridge plug assembly (referred to herein as a "plug") downhole of a well section or interval to be perforated and fractured. Positioning of the plug may be aided by pumping a driving fluid through the well. This may be particularly helpful where the plug is being advanced through a horizontal section of the well.

Once in place, equipment may communicate with the plug so as to direct setting of the plug. Such setting may include expanding slips and one or more seal members of the plug for anchoring and sealing of the plug, respectively. Once anchored and sealed, a perforation application may take place above the plug so as to provide perforations through the casing in the well interval. Similarly, a fracturing application may follow that directs fracturing fluid under high pressure through the casing perforations and into the adjacent formation, which causes hydraulic fracturing of the reservoir rock of the adjacent formation that is intended to release oil or gas trapped in the reservoir rock such that it flows into the well for easier production. The fracturing fluid typically contains a proppant (such as sand) that aids in holding the fractures open after the fracturing application has been completed. This process may be repeated, generally starting from the terminal end (e.g., toe end) of the well and moving uphole interval by interval, until the casing and formation have been configured and treated as desired.

The presence of the plug in the well keeps the high pressure fracturing applications from affecting the well interval below the plug. Indeed, even though the noted applications are likely to generate well over 5,000 psi, the well interval below the plug is kept hydraulically isolated from the interval thereabove. Due to the high pressure nature of the fracturing and the degree of anchoring required of the plug, it is generally configured for near permanent placement once set. As a result, removal of the plug requires follow on milling out of the plug. Depending on the particular architecture of the well, several plug mill-outs may take place over the course of conventional perforating and fracturing applications for a given well.

As noted above, it is commonplace for a well to be partitioned into a number of intervals. Short sections of unperforated casing can be located between intervals to enable the plugs to be set for isolation of the respective intervals for perforation and fracturing of the respective intervals. Note that not all intervals of the well can contribute equally to the production of hydrocarbons from the well as the petrophysical and geomechanical properties of the reservoir can vary along the length of the well.

Current workflows used to evaluate the productivity of individual intervals of the well are based on two main techniques. The first workflow, commonly described as production logging, is based on the downhole measurements of fluid properties using spinners and pressure measurement. This first workflow requires a tool to be run in the well after milling-out all of the plugs, thus increasing the cost of the well. The second workflow is based on the measurement of tracer concentration. Different tracers are injected into the reservoir with the fracturing fluid over the intervals of the well. The tracers are produced from well with the fracturing fluid and/or hydrocarbons during the initial production of the well. The amount of each given tracer that is produced is a function of the flow contribution of the respective interval in which the given tracer was placed. The use of the multiple different tracers allows for the evaluation of the flow contributions over the number of intervals of the well. Beyond the limitation inherent to the interpretation of the produced fluids (including the tracers, the fracturing fluid and/or hydrocarbons), this second workflow has a limitation in the number of tracers that can be placed into the intervals of a single well as well as the detection of the tracers in the produced fluids.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

Illustrative embodiments of the present disclosure are directed to a method and system for characterizing a hydraulically-fractured hydrocarbon-bearing formation that is traversed by a well having a number of intervals that are hydraulically isolated from one another by corresponding plugs. The method and system analyzes flow characteristics of return fluid that flows from a newly-opened well interval back to a surface-located facility during plug mill-out operations. Local formation properties of the formation adjacent the newly-opened well interval can be determined based upon the flow characteristics of the return fluid. The local formation properties can include fracture area, fracture conductivity, fracture connectivity with wellbore, fracture geometry, formation pressure, formation productivity and/or other suitable formation properties.

The fracture connectivity can represent whether or not the newly-opened well interval (i.e., the wellbore interval between the newly opened plug and the next downstream plug) is in communication with the local region of the formation adjacent the newly-opened well interval. In other words, the fracture connectivity can represent whether or not the hydraulic fractures that were created by hydraulic fracturing of the well interval (now newly-opened) still connect the well interval to the reservoir.

The fracture connectivity can also represent the number of fractures (or fracture clusters) in communication with the local region of the formation adjacent the newly-opened well interval. In other words, the fracture connectivity can represent the number of fractures (or fracture clusters) that were created by hydraulic fracturing of the well interval (now newly-opened) that still connect the well interval to the reservoir.

The local formation properties can also represent whether or not the fractures that were created by hydraulic fracturing of the well interval (now newly-opened) provide fluid communication (such as behind-the-casing fluid communication) with the fractures of a neighboring well interval.

The local formation properties can also represent whether or not the local region of the formation that is connected to the newly-opened well interval by fractures is normally-pressured, over-pressured or under-pressured (which is an indication of a depleted zone).

The local formation properties can also represent whether or not the local region of the formation that is connected to the newly-opened well interval by fractures is overbalanced or underbalanced with respect to the wellbore at the time of the mill-out operations.

The local formation properties can also represent whether or not the local region of the formation that is connected to the newly-opened well interval by fractures is prone to either proppant production, formation failure of both.

The local formation properties can also represent wettability and propensity to fluid leakoff and imbibition for the local region of the formation that is connected to the newly-opened well interval by fractures.

The local formation properties can also represent rock quality of the formation, such as porosity, hydrocarbon content, mineralogy, and formation toughness, lamination density, and density of natural/induced fractures.

The local formation properties can also represent mechanical properties of the formation, such as stress, Young modulus, and Poison ratio.

In one or more embodiments, the flow characteristics of the return fluid can be derived from the output of a surface-located multiphase flow meter.

In one or more embodiments, the return fluid can include milling fluid that is supplied to a downhole milling bit. In one embodiment, the hydrostatic pressure of the milling fluid supplied to the downhole milling bit can be greater than formation pressure. In this case, the analyzing of the flow characteristics of the return fluid can account for an outflow of milling fluid into fractures of the newly-opened well interval. In another embodiment, the hydrostatic pressure of the milling fluid supplied to the downhole milling bit can be less than formation pressure. In this case, the analyzing of the flow characteristics of the return fluid can account for an inflow of water (including water-based fracturing fluid and connate water), oil, gas and solids from fractures of the newly-opened well interval.

In one or more embodiments, the milling fluid can include a tracer compound (or multiple tracer compounds) to help quantitatively distinguish the milling fluid from produced fluids (including fracturing fluid, connate water, and oil and gas hydrocarbons). The tracer compound(s) can be added to the milling fluid continuously or in pulses. A surface-located chemical analyzer can measure concentration of the tracer compound(s) in return fluid that flows to the surface in order to discriminate between sources and sinks of milling fluid and/or reservoir fluids during the plug mill-out operations. The concentration of the tracer compound(s) can be varied in a controlled manner in conjunction with controlled pressure variations of the milling fluid supplied to the milling bit during plug mill-out operations in order to discriminate between sources and sinks of reservoir fluids during the plug mill-out operations.

In one or more embodiments, a tracer compound (or multiple tracer compounds) can be incorporated into the fracturing fluid used to fracture the formation. The tracer compound(s) of the fracturing fluid can help quantitatively distinguish the fracturing fluid from the milling fluid and/or other produced fluids (such as connate water). A surface-located chemical analyzer can measure concentration of the tracer compound(s) in return fluid that flows to the surface in order to discriminate between sources and sinks of reservoir fluids during the plug mill-out operations.

In one or more embodiments, the pumping rate of the milling fluid can be controlled such that the return rate of the return fluid is maintained within a range that is intended to maintain substantial stability of proppant pack in the fractures of the opened interval(s) of the well during the plug drill-out operations or enables control over proppant flowback from the fractures of the opened interval(s) of the well during the plug drill-out operations.

In other embodiments, the method and system can analyze flow characteristics of return fluid that flows to a surface-located facility during well cleanout or workover operations. Cleanout or workover fluid can be pumped downhole during well cleanout or workover operations. The cleanout or workover fluid can incorporate one or more tracer compounds as described herein. Local formation properties can be determined based upon the surface flow characteristics of the return fluid during the well cleanout or workover operations in a manner similar to the plug mill-out operations as described herein.

BRIEF DESCRIPTION OF THE DRAWINGS

FIGS. 1A and 1B are schematic illustrations of an oilfield well that traverses a hydraulically-fractured hydrocarbon-bearing reservoir as well as a downhole tool for milling out plugs that isolate a number of intervals offset from one another along the length of the well.

DETAILED DESCRIPTION

Figure 1B:
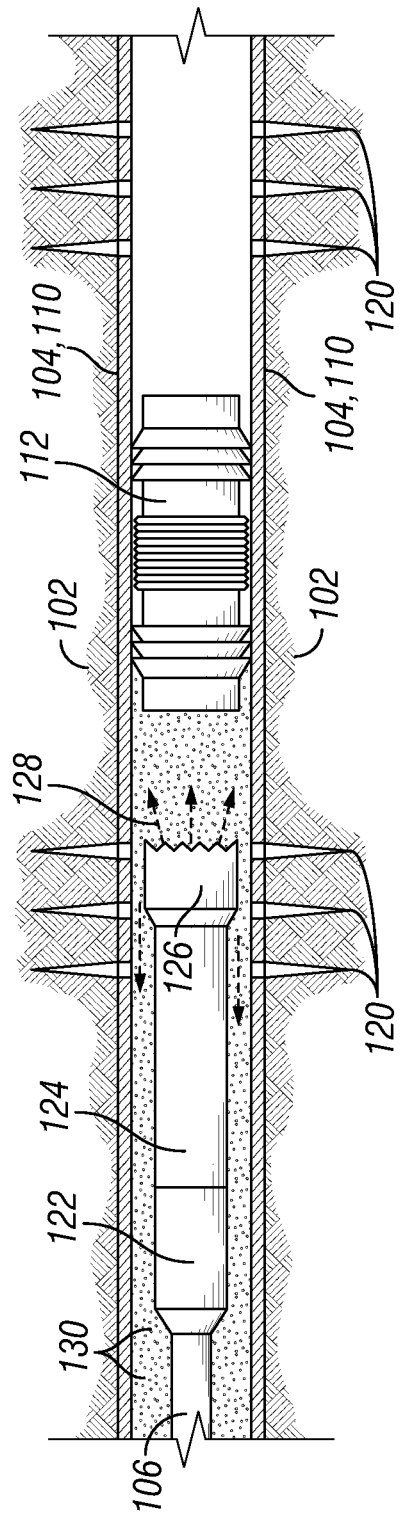

Illustrative embodiments of the present disclosure are described below. In the interest of clarity, not all features of an actual implementation are described in this specification. It will be appreciated that in the development of any such actual embodiment, numerous implementation-specific decisions must be made to achieve the developer's specific goals, such as compliance with system-related and business-related constraints, which will vary from one implementation to another. Moreover, it will be appreciated that such a development effort might be complex and time-consuming but would nevertheless be a routine undertaking for those of ordinary skill in the art having the benefit of this disclosure. Further, like reference numbers and designations in the various drawings indicate like elements.

Certain examples are shown in the above-identified figures and described in detail below. In describing these examples, like or identical reference numbers are used to identify common or similar elements. The figures are not necessarily to scale and certain features and certain views of the figures may be shown exaggerated in scale or in schematic for clarity and/or conciseness.

"Above", "upper", "upstream", "heel" and like terms in reference to a well, wellbore, tool, or formation refer to the relative direction or location near or going toward or on the surface side of the device, item, flow or other reference point, whereas "below", "lower", "downstream", "toe" and like terms refer to the relative direction or location near or going toward or on the bottom hole side of the device, item, flow or other reference point, regardless of the actual physical orientation of the well or wellbore, e.g., in vertical, horizontal, downwardly and/or upwardly sloped sections thereof.

As used herein, an opened interval or newly-opened interval refers to a section of a well with at least one perforation, perforation cluster, a jetted hole in the casing, a slot, at least one sliding sleeve or wellbore casing valve, or any other opening in the production tubing that provides communication between the formation and the wellbore. The opened interval(s) or newly-opened interval(s) of the well can be partitioned into one or more perforated zones.

As used herein, a fracture shall be understood as one or more cracks or surfaces of breakage within rock. Fractures can enhance permeability of rocks greatly by connecting pores together, and for that reason, fractures are induced mechanically in some reservoirs in order to boost hydrocarbon flow. Fractures may also be referred to as natural fractures to distinguish them from fractures induced as part of a reservoir stimulation. Fractures can also be grouped into fracture clusters (or "perf clusters") where the fractures of a given fracture cluster (perf cluster) connect to the wellbore through a single perforated zone.

The term "fracturing" refers to the process and methods of breaking down a geological formation and creating a fracture, i.e. the rock formation around a well bore, by pumping fluid at very high pressures (pressure above the determined closure pressure of the formation), in order to increase production rates from a hydrocarbon reservoir. The fracturing applications described herein otherwise use conventional techniques known in the art.

FIGS. 1A and 1B show an example well 100 that has undergone perforation and fracturing applications. In this well, a platform and derrick 116 is positioned over a wellbore 112 that traverses a hydrocarbon-bearing reservoir 102 by rotary drilling. While certain elements of the well 100 are illustrated in FIGS. 1A and 1B, other elements of the well (e.g., blow-out preventers, wellhead "tree", etc.) have been omitted for clarity of illustration. The well 100 includes an interconnection of pipes, including vertical and horizontal casing 104, tubing 106 (which can be coiled tubing or drill pipe), transition 108, and a production liner 110 that connect to a surface facility (FIG. 2) at the surface 101. The tubing 106 extends inside the casing 104 and terminates at a tubing head (not shown) at or near the surface 101. The casing 104 contacts the wellbore 112 and terminates at a casing head (not shown) at or near the surface 101. The production liner 110 and/or horizontal casing 104 have aligned radial openings termed "perforation zones" 120 that allow fluid communication between the production liner 110 and the hydraulically fractured hydrocarbon-bearing reservoir or formation 102. A number of plugs 112 are disposed in the well 100 at positions offset from one another along the length of the well in order to provide hydraulic isolation between certain intervals of the well 100 with a number of perforation zones 120 in each interval. Each plug 112 can include one or more expanding slips and seal members for anchoring and sealing the plug to the production liner 110 or casing 104 as is conventional. Each plug 112 can be formed primarily from composite materials (or other suitable materials) that enables the plug to be milled-out for removal as described herein.

A bottom hole assembly ("BHA") 122 may be run inside casing 104 by tubing 106 (which can be coiled tubing or drill pipe). As shown in FIG. 1B, the BHA 122 includes a downhole motor 124 that operates to rotate a milling bit 126.

Figure 2:
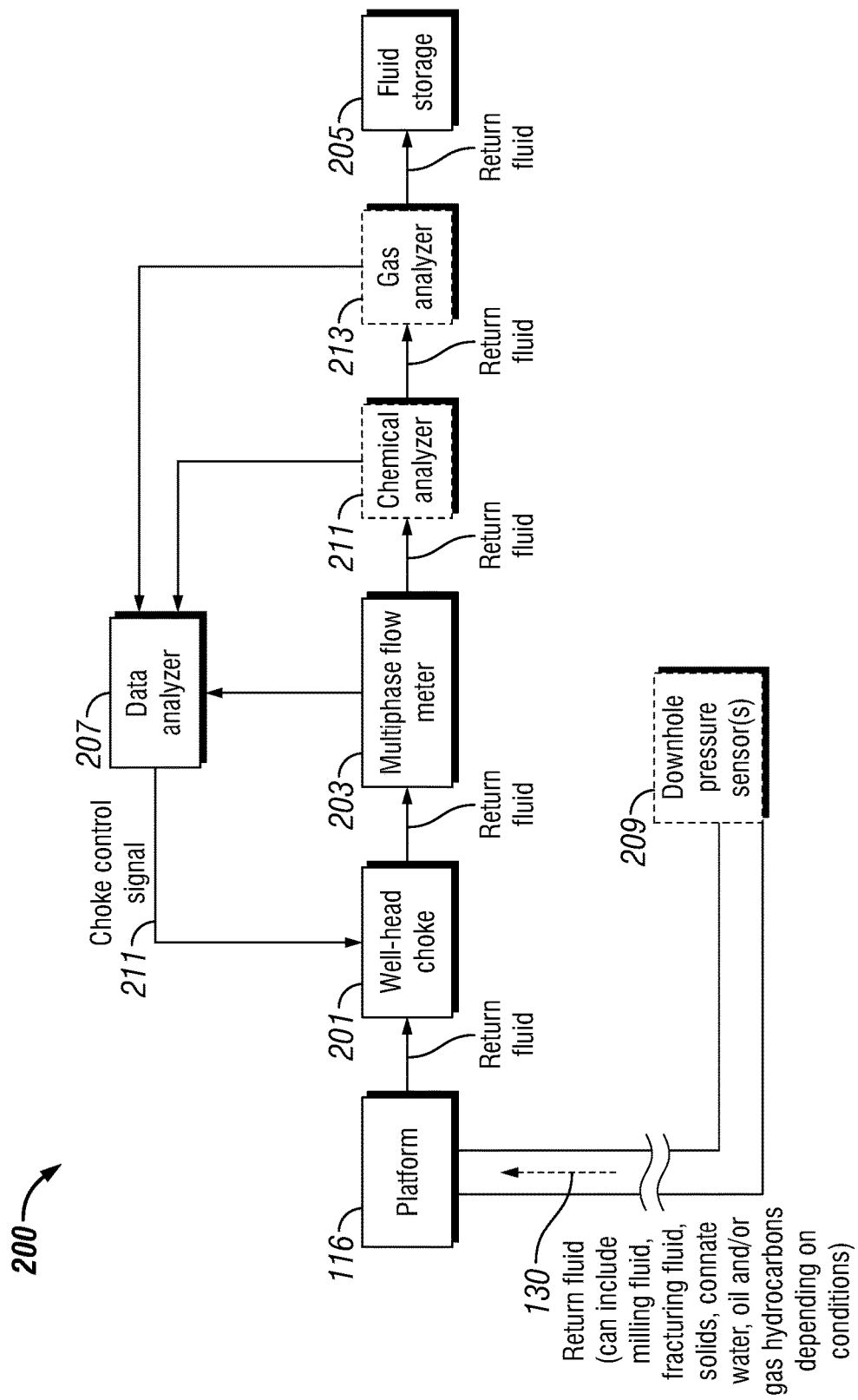
FIG. 2 is a functional block diagram of a surface facility that analyzes flow characteristics of return fluid that flows from a newly-opened well interval back to the surface during plug mill-out operations in order to characterize local properties of the formation adjacent the newly-opened well interval.

The downhole motor 124 can be driven by hydraulic forces carried in milling fluid supplied from the surface. Downhole motors are well known in the art. The BHA 122 is connected to the tubing 106, which is used to run the BHA 122 to a desired location within the well. It is also contemplated that the rotary motion of the milling bit 126 can be driven by rotation of the tubing 106 effectuated by a rotary table or other surface-located rotary actuator. In this case, the downhole motor 124 can be omitted. The tubing 106 can also be used to deliver milling fluid (arrows 128A) to the milling bit 126 to aid in the milling process and carry cuttings and possibly other fluid and solid components in fluid 130 (referred to herein as "return fluid") that flows up the annulus between the tubing 106 and the casing 104 (or via a return flow path provided by the tubing 106) for return to the surface facility (FIG. 2). The BHA 122 can be located such that the milling bit 126 is positioned in direct contact with the plug 112. In this configuration, the rotary motion of the milling bit 126 mills away the plug 112 into cuttings that flow as part of the return fluid 130 that is returned to the surface facility. It is also contemplated that the return fluid 130 can include remnant proppant (e.g., sand) or possibly rock fragments that result from the hydraulic fracturing application and flow within the well during the plug mill-out process. After the hydraulic isolation provided a plug is removed by the milling, a flow path is opened past the drill plug. Under certain conditions, fracturing fluid and possibly hydrocarbons (oil and/or gas), proppants and possibly rock fragments can flow from the fractured reservoir 102 through the perforations 120 in the newly opened interval and back to the surface as part of the return fluid 130. In embodiments, the BHA may be supplemented behind the rotary drill by an isolation device such as for example an inflatable packer that can be activated to isolate the zone below or above it and enable local pressure tests.

As shown in FIG. 2, the surface facility 200 includes a well-head choke 201, a multiphase flow meter 203, fluid storage 205, and a data analyzer 207. One or more optional downhole pressure sensor(s) 209 may also be included. The downhole pressure sensor(s) 209 can be integral to the milling tool BHA 122, the tubing 106 that is used to run in the milling tool BHA 122, the production liner 110 or horizontal casing 104, or some other part of the well completion. In embodiments, the downhole pressure may be computed from surface pressure, known fluid composition, depth and known parameters of friction pressure. The return fluid 130 flows from the platform 130 through the multiphase flow meter 203 for storage in fluid storage 205. The return fluid stored in the fluid storage 205 can possibly be reclaimed for reuse in subsequent milling operations, if desired. The multiphase flow meter 203 can be configured to measure the flow rates of different phases (e.g., oil, gas, water, solids) that make up the return fluid 130 that returns to the surface during the mill-out operations. The oil and gas phases of the return fluid 103 can originate from hydrocarbons that flow from the hydraulically-fractured formation 102 through the perforations 120 and back to the surface as part of the return fluid 130. The oil phase of the return fluid 130 can also possibly originate from oil-based milling fluid that is supplied to the downhole milling bit 126. The water phase of the return fluid 103 can originate from water-based milling fluid that is supplied to the downhole milling bit 126 and/or from water-based fracturing fluid and/or connate water that flows from the hydraulically-fractured formation 102 through the perforations 120 and back to the surface as part of the return fluid 130. The solid phase of the return fluid 103 can originate from remnant proppant (e.g., sand) or possibly rock fragments that result from the hydraulic fracturing application and flow within the well during the mill-out operations.

The data analyzer 207 interfaces to the multiphase flow meter 203 and possibly the downhole pressure sensor(s) 209 via suitable data communication links (such as wired electrical communication links, wireless RF communication links, or optical communication links). The surface-located multiphase flow meter 203 can be configured to measure flow rates of the various phases (oil/gas/water/solid) of the stream of return fluid 130 produced from the well in real time. In one embodiment, the multiphase flow meter 203 may be a Model Vx Spectra multiphase flow meter supplied by Schlumberger Limited of Sugarland, Tex. The data analyzer 207 can be configured to process the multiphase flow rate measurements of the return fluid 130 carried out by the surface-located multiphase flow meter 203 and pressure measurements carried out by the optional downhole pressure sensor(s) 209 during the mill-out operations of a particular plug in order to characterize the flow contributions of one or more different fluid phases that flow through perforation zone(s) of the well interval corresponding to the particular plug (i.e., the newly-opened well interval that was hydraulically isolated by the particular plug before being milled out). Such flow contributions can characterize the flow rates of milling fluid, water (including water-based fracturing fluid and/or connate water), oil and/or gas that flows through the perforation zone(s) of the newly-opened well interval. During the mill-out operation of the particular plug, the data analyzer 207 can determine such flow contributions of the newly-opened well interval using nodal analysis and modeling of the multiphase flow rate measurements of the return fluid 130 carried out by the multiphase flow meter 203 and optional downhole pressure measurements carried out by the downhole pressure sensor(s) 209. Note that after mill-out of the particular plug, the open wellbore length increases by the length of the newly-opened well interval. Such nodal analysis and modeling can be used to characterize the effective open wellbore length after mill-out of the plug. The flow contributions of one or more different fluid phases that flow through the perforation zone(s) of the newly-opened well interval and the effective open wellbore length after mill-out can be used to characterize local properties of the formation 102 adjacent the newly-opened well interval for reservoir analysis and/or planning. For example, such local formation properties can include fracture area and/or fracture conductivity of the formation adjacent the newly-opened well interval, fracture connectivity with the wellbore, fracture geometry, formation pressure, formation productivity or other suitable formation properties. This process can be repeated when milling out the other plugs in the well in order to characterize local formation properties adjacent other intervals-of-interest along the length of the well.

The fracture connectivity can represent whether or not the newly-opened well interval (i.e., the wellbore interval between the newly opened plug and the next downstream plug) is in communication with the local region of the formation adjacent the newly-opened well interval. In other words, the fracture connectivity can represent whether or not the hydraulic fractures that were created by hydraulic fracturing of the well interval (now newly-opened) still connect the well interval to the reservoir. The fracture connectivity can also represent the number of fractures (or fracture clusters) in communication with the local region of the formation adjacent the newly-opened well interval. In other words, the fracture connectivity can represent the number of fractures (or fracture clusters) that were created by hydraulic fracturing of the well interval (now newly-opened) that still connect the well interval to the reservoir.

The local formation properties can also represent whether or not the fractures that were created by hydraulic fracturing of the well interval (now newly-opened) provide fluid communication (such as behind-the-casing fluid communication) with the fractures of a neighboring well interval. The local formation properties can also represent if the local region of the formation that is connected to the newly-opened well interval by fractures is normally-pressured, over-pressured or under-pressured (which is an indication of a depleted zone).

The local formation properties can also represent if the local region of the formation that is connected to the newly-opened well interval by fractures is overbalanced or underbalanced with respect to the wellbore at the time of the mill-out operations.

The local formation properties can also represent if the local region of the formation that is connected to the newly-opened well interval by fractures is prone to either proppant production, formation failure of both.

The local formation properties can also represent wettability and propensity to fluid leakoff and imbibition for the local region of the formation that is connected to the newly-opened well interval by fractures.

The local formation properties can also represent rock quality of the formation, such as porosity, hydrocarbon content, mineralogy, and formation toughness, lamination density, and density of natural/induced fractures.

The local formation properties can also represent mechanical properties of the formation, such as stress, Young modulus, and Poison ratio.

The characterization of each interval can be used to optimize a subsequent flowback program as expected outflow rates will depend on the number of intervals that contribute to production and the magnitude of their respective contribution. Subsequent to the mill-out and the flowback program, the characterization of the intervals can provide a first estimate of the well productivity and can serve as the basis for evaluating the need for artificial lift and its design. A certain interval that exhibits one or more local formation properties (e.g., fracture area/conductivity) that indicate unfavorable stimulation can be expected to contribute little to hydrocarbon production yet contribute to excessive solids production that can impact the hydrocarbon production from other intervals. Such an interval can be bypassed by chemical treatment or the like, or possibly flagged for immediate or remedial stimulation.

Figure 3:
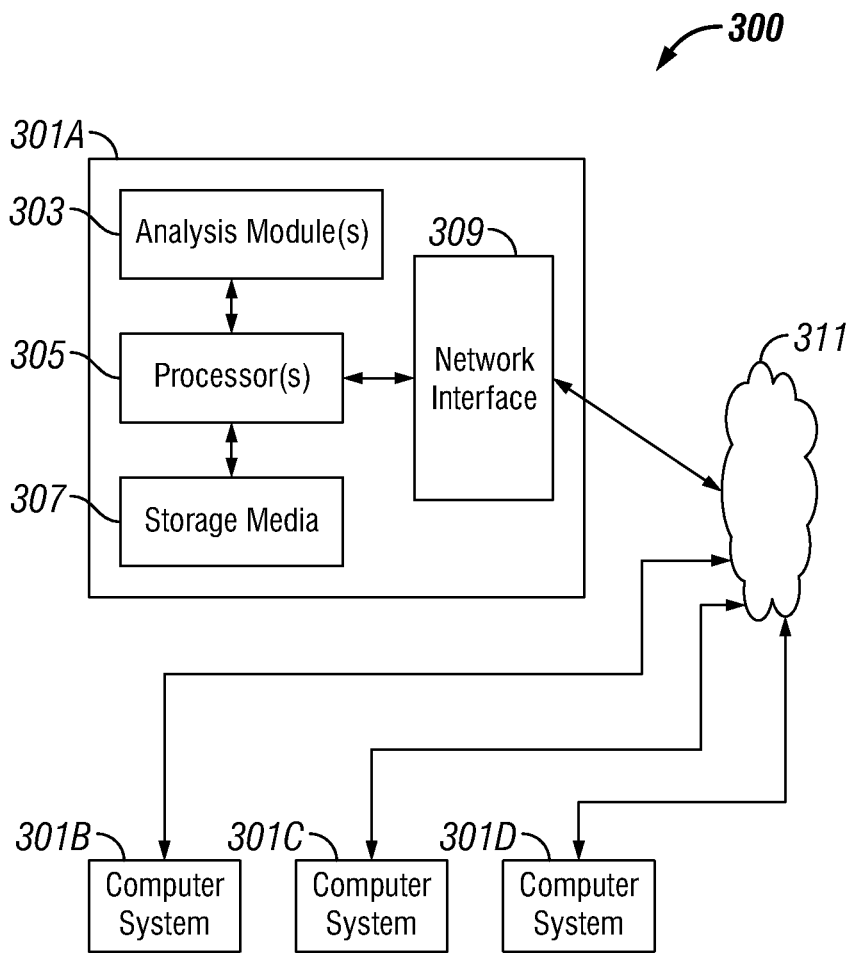
FIG. 3 shows an example computing system that can be used to implement the data analyzer of FIG. 2.

FIG. 3 shows an example computing system 300 that can be used to implement the data analyzer 207 of FIG. 2 or parts thereof. The computing system 300 can be an individual computer system 301A or an arrangement of distributed computer systems. The computer system 301A includes one or more analysis modules 303 (a program of computer-executable instructions and associated data) that can be configured to perform various tasks according to some embodiments, such as the tasks described above. To perform these various tasks, an analysis module 303 executes on one or more processors 305, which is (or are) connected to one or more storage media 307. The processor(s) 305 is (or are) also connected to a network interface 309 to allow the computer system 301A to communicate over a data network 311 with one or more additional computer systems and/or computing systems, such as 301B, 301C, and/or 301D. Note that computer systems 301B, 301C and/or 301D may or may not share the same architecture as computer system 301A, and may be located in different physical locations.

The processor 305 can include at least a microprocessor, microcontroller, processor module or subsystem, programmable integrated circuit, programmable gate array, digital signal processor (DSP), or another control or computing device.

The storage media 307 can be implemented as one or more non-transitory computer-readable or machine-readable storage media. Note that while in the embodiment of FIG. 3, the storage media 307 is depicted as within computer system 301A, in some embodiments, storage media 307 may be distributed within and/or across multiple internal and/or external enclosures of computing system 301A and/or additional computing systems. Storage media 307 may include one or more different forms of memory including semiconductor memory devices such as dynamic or static random access memories (DRAMs or SRAMs), erasable and programmable read-only memories (EPROMs), electrically erasable and programmable read-only memories (EEPROMs) and flash memories; magnetic disks such as fixed, floppy and removable disks; other magnetic media including tape; optical media such as compact disks (CDs) or digital video disks (DVDs); or other types of storage devices. Note that the computer-executable instructions and associated data of the analysis module(s) 303 can be provided on one computer-readable or machine-readable storage medium of the storage media 307, or alternatively, can be provided on multiple computer-readable or machine-readable storage media distributed in a large system having possibly plural nodes. Such computer-readable or machine-readable storage medium or media is (are) considered to be part of an article (or article of manufacture). An article or article of manufacture can refer to any manufactured single component or multiple components. The storage medium or media can be located either in the machine running the machine-readable instructions, or located at a remote site from which machine-readable instructions can be downloaded over a network for execution.

It should be appreciated that computing system 300 is only one example of a computing system, and that computing system 300 may have more or fewer components than shown, may combine additional components not depicted in the embodiment of FIG. 3, and/or computing system 300 may have a different configuration or arrangement of the components depicted in FIG. 3. The various components shown in FIG. 3 may be implemented in hardware, software, or a combination of both hardware and software, including one or more signal processing and/or application specific integrated circuits.

Further, the operations of the data analyzer 207 as described herein may be implemented by running one or more functional modules in an information processing apparatus such as general purpose processors or application specific chips, such as ASICs, FPGAs, PLDs, SOCs, or other appropriate devices. These modules, combinations of these modules, and/or their combination with general hardware are all included within the scope of the disclosure.

Figure 4A:
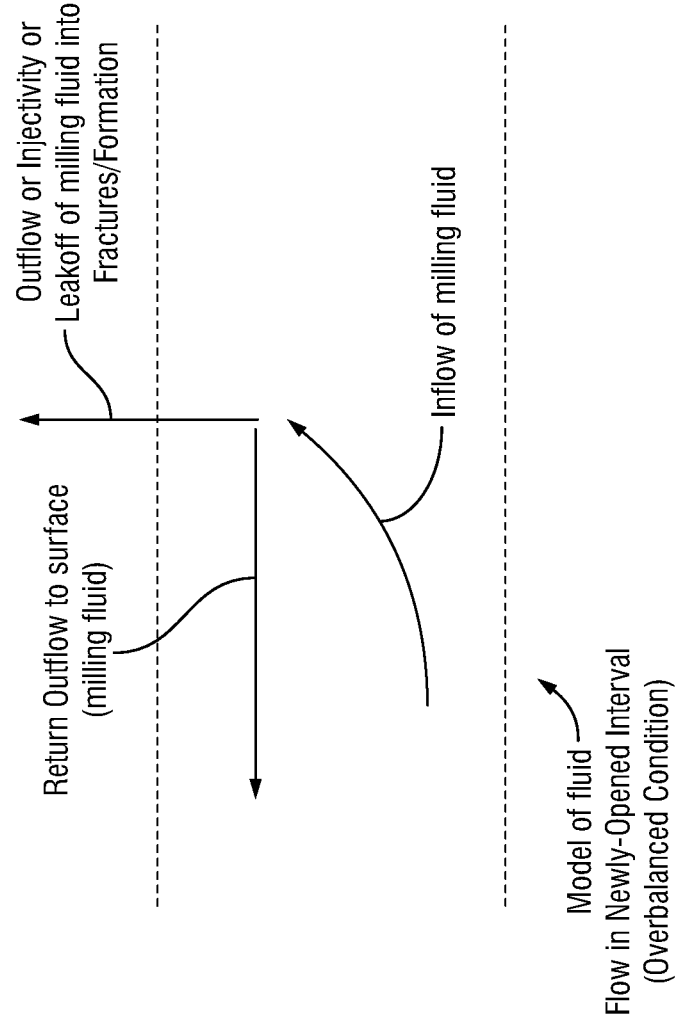
FIG. 4A is a schematic illustration of a fluid model that models fluid flow in a newly-opened well interval during mill-out for an overbalanced condition where the hydrostatic pressure of the milling fluid supplied to the milling bit is greater than the formation pressure.

In one embodiment, the hydrostatic pressure of the milling fluid supplied to the milling bit 126 during the mill-out operation of a particular plug 120 can be greater than the formation pressure, which is mainly dictated by the pressure of fracturing fluid injected into the formation 102 during the fracturing operations. In this overbalanced condition, when the hydraulic isolation provided by the particular plug is removed by the milling, the milling fluid has a tendency to flow through the perforation zone(s) of the newly-opened well interval and into the adjacent formation 102. In this case, the nodal analysis and modeling carried out by data analyzer 207 can account for the inflow of milling fluid supplied to the milling bit 126 for the newly-opened interval, the outflow or leakoff of milling fluid into the fractures and/or formation (referred to herein as "injectivity") for the newly-opened interval, and the return outflow of fluid from the newly-opened interval that returns to the surface as shown in FIG. 4A. Note that the flow rate output of the surface-located multiphase flow meter 201 for the phase corresponding to the milling fluid supplied to the milling bit 126 can be used by the nodal analysis and modeling to characterize the contribution of the return outflow from the newly-opened interval as part of the return fluid 130 that returns to the surface as well as the injectivity of milling fluid into the fractures and/or formation for the newly-opened interval. Thus, if water-based milling fluid is used, the water phase flow rate as measured by the surface-located multiphase flow meter 201 can be used in the analysis and modeling. On the other hand, if oil-based milling fluid is used, the oil phase flow rate as measured by the surface-located multiphase flow meter 201 can be used in the analysis and modeling. Once characterized, the injectivity for the newly-opened interval can be related to one or more local formation properties of the formation adjacent the newly-opened interval as described herein by correlation, modeling or other suitable techniques. Such local formation property(ies) can be evaluated to determine good fractures or poor/failed fractures for the newly-opened interval. The solid phase flow rate as measured by the surface-located multiphase flow meter 201 can also be used to identify good fractures or poor/failed fractures for the newly-opened interval where excessive solids production provides an indication of poor/failed fractures. Such excessive solids production can also indicate solids in the well over the newly-opened interval.

Figure 4B:
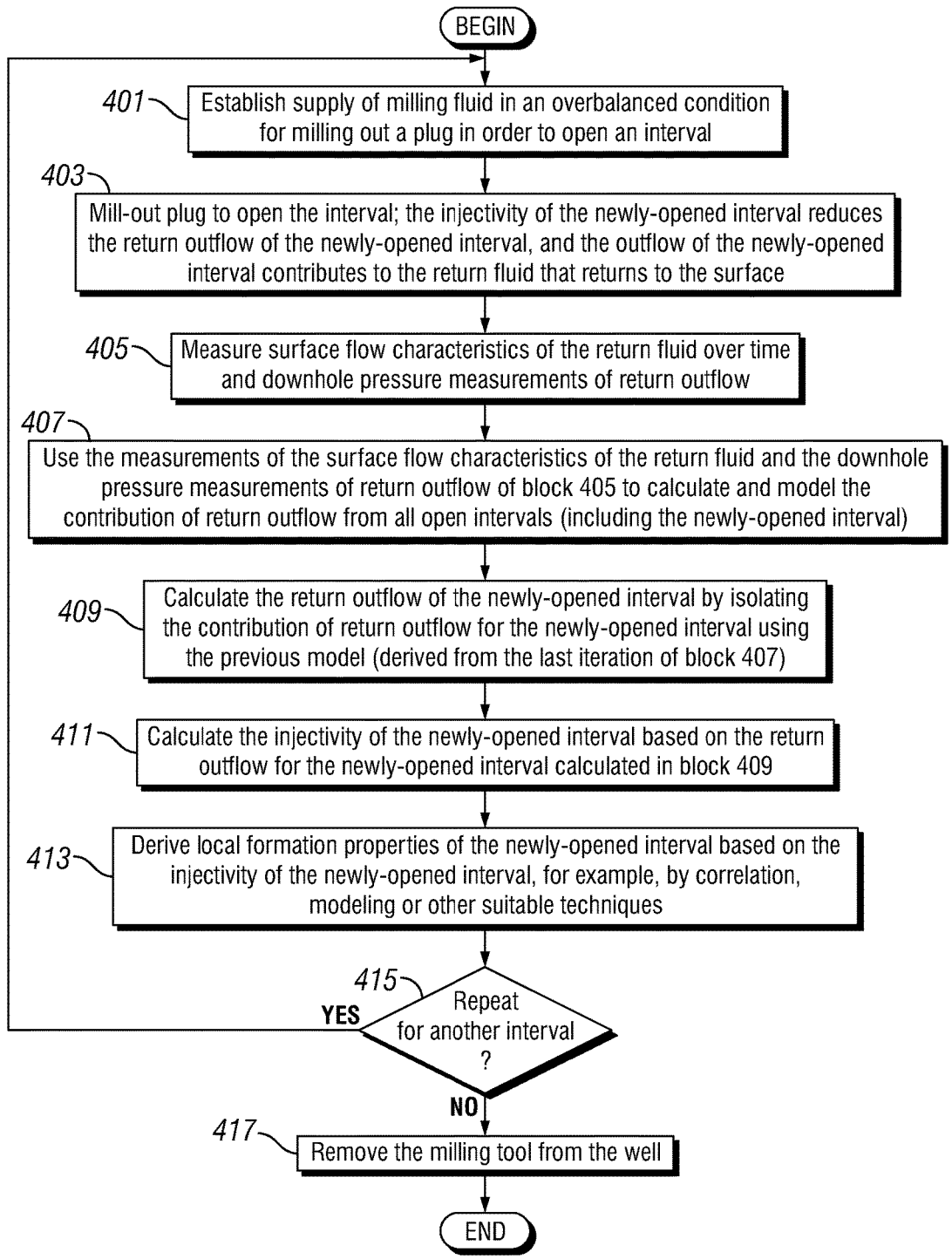
FIG. 4B is a flowchart illustrating exemplary operations carried out by the data analyzer of FIG. 2 that uses the fluid model of FIG. 4A to analyze the flow characteristics of return fluid during plug mill-out operations for the overbalanced condition in order to characterize local properties of the formation adjacent the newly-opened well interval.

FIG. 4B illustrates a workflow carried out by the data analyzer 207 of FIG. 2 that uses the fluid model of FIG. 4A to analyze the flow characteristics of return fluid during plug mill-out operations for the overbalanced condition in order to characterize local properties of the formation adjacent the newly-opened well interval. The workflow begins in block 401 where the supply of milling fluid in an overbalanced condition is established to power and lubricate the milling tool BHA 122 for milling out a plug in order to open a well interval. In block 403, the milling tool BHA 122 is operated to mill-out the plug to open the interval. In this case, the injectivity of the newly-opened interval reduces the return outflow of the newly-opened interval, and the return outflow of the newly-opened interval contributes to the return fluid 130 that returns to the surface. In block 405, with the milling tool BHA 122 located in the newly-opened interval and the return outflow from the newly-opened interval contributing to the return fluid 130 at the surface, the data analyzer 207 can measure surface flow characteristics of the return fluid 130 over time and downhole pressure characteristics of the return outflow of the newly-opened interval. In block 407, the data analyzer 207 uses the measurements of the surface flow characteristics of the return fluid 130 and the downhole pressure measurements of return outflow of block 405 to calculate and model the return outflow from all open intervals (including the newly-opened interval) that is part of the return fluid that returns to the surface. Note that the model of block 407 is a combination or convolution of the return outflow from all open intervals (including the newly-opened interval) of the well, and these open intervals are different over the sequence of well intervals that are opened by the plug mill-out operations. In block 409, the data analyzer 207 calculates the return outflow of the newly-opened interval by isolating the contribution of return outflow for the newly-opened interval from the previous model (derived from the last iteration of block 407). The calculations of block 409 can involve subtracting the return outflow from the previous model (derived from the last iteration of block 407) from the return outflow of the model derived in block 405. In block 411, the data analyzer 207 calculates the injectivity of the newly-opened interval based on the return outflow for the newly-opened interval calculated in block 409. In block 413, the data analyzer 207 derives local formation properties of the newly-opened interval based on the injectivity of the newly-opened interval as calculated in block 411, for example, by correlation, modeling or other suitable techniques. In block 415, it is determined whether the plug mill-out and corresponding data analysis operations of blocks 401 to 413 should be repeated to open and characterize another interval of the well. The determination of block 415 can be performed in an automated manner by computer evaluation of one or more predefined conditions, in a manual manner by human analysis of the data or in a semi-automated manner involving both computer evaluation and human analysis. If so, the workflow continues to block 401 to repeat blocks 401 to 413 for another interval of the well. Otherwise, the milling tool BHA 122 can be removed from the well in block 417 and the workflow ends.

Note that as each plug is milled out, the new measurements of surface flow characteristics and downhole pressure measurements are used to update the calculations and model of block 407. Changes to the model between before and after the mill-out of each plug can be used to isolate the contribution of return outflow for the newly-opened interval in block 409 and derive injectivity of the newly-opened interval in block 411 and local formation properties based thereon in block 413. The sequence of well intervals that are opened by plug mill-out operations according to the workflow of FIG. 4B can be varied as desired. For example, the plugs can be milled out and corresponding intervals opened and characterized interval-by-interval from the heel to the toe of the well (or from the toe to the heel of the well).

Figure 5A:
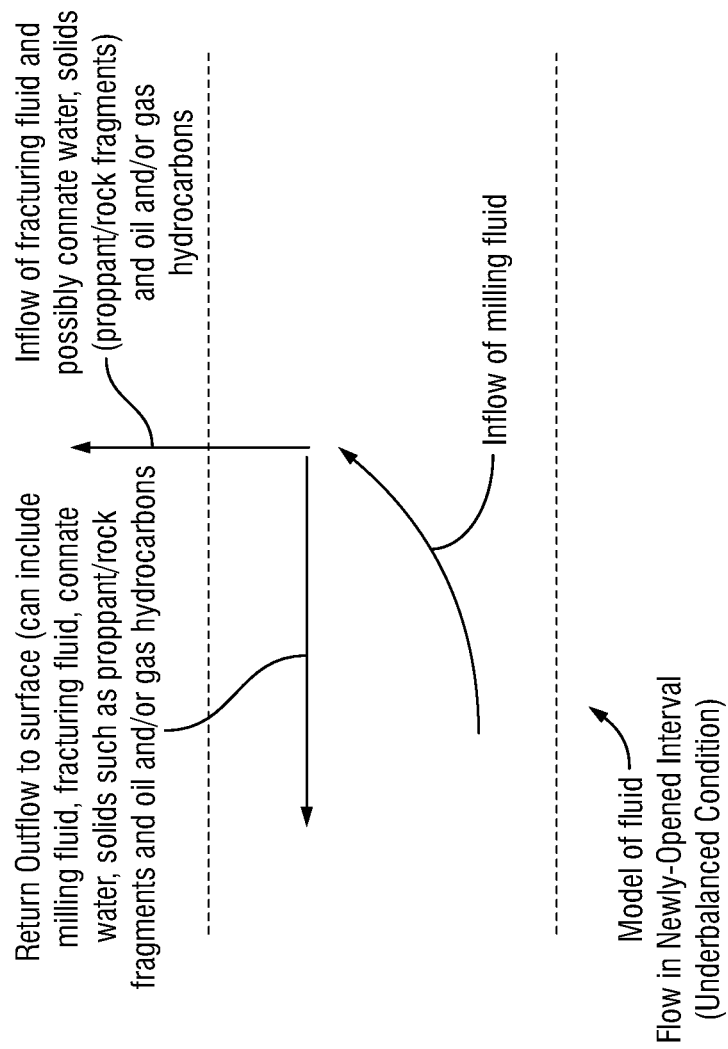
FIG. 5A is a schematic illustration of a fluid model that models fluid flow in a newly-opened well interval during mill-out for an underbalanced condition where the hydrostatic pressure of the milling fluid supplied to the milling bit is less than the formation pressure.

In another embodiment, the hydrostatic pressure of the milling fluid supplied to the milling bit 126 during the mill-out operation of a particular plug 120 can be less than the formation pressure, which is mainly dictated by the pressure of fracturing fluid injected into the formation 102 during the fracturing operations. In this underbalanced condition, when the hydraulic isolation provided by the particular plug is removed by the milling, water (including water-based fracturing fluid and/or connate water) along with possibly solids (including proppant or rock fragments) and oil and/or gas hydrocarbons held in the fractures and adjacent formation 102 have a tendency to flow through the perforation zone(s) of the newly-opened interval and into the well and to the surface. In this case, the nodal analysis and modeling carried out by data analyzer 207 can account for the inflow of milling fluid supplied to the milling bit 126 for the newly-opened interval, the inflow of water, oil and/or gas hydrocarbons and solids for the newly-opened interval, and the return outflow from the interval to the surface as shown in FIG. 5A. Note that the water phase flow rate output of the surface-located multiphase flow meter 201 can be used by the nodal analysis and modeling to characterize the inflow of water (including water-based fracturing fluid and/or connate water) for the newly-opened interval. The oil phase flow rate output of the surface-located multiphase flow meter 201 can be used by the nodal analysis and modeling to characterize the inflow of oil for the newly-opened interval. The gas phase flow rate output of the surface-located multiphase flow meter 201 can be used by the nodal analysis and modeling to characterize the inflow of gas for the newly-opened interval. Once characterized, the in-flow of water, oil and/or gas for the newly-opened interval can be related to one or more local formation properties of the formation adjacent the newly-opened interval as described herein by correlation, modeling or other suitable techniques. Such local formation property(ies) can be evaluated to determine good fractures or poor/failed fractures for the newly-opened interval. The solid phase flow rate as measured by the surface-located multiphase flow meter 201 can also be used to identify good fractures or poor/failed fractures for the interval where excessive solids production provides an indication of poor/failed fractures. Such excessive solids production can indicate solids in the well over the newly-opened interval.

Figure 5B:
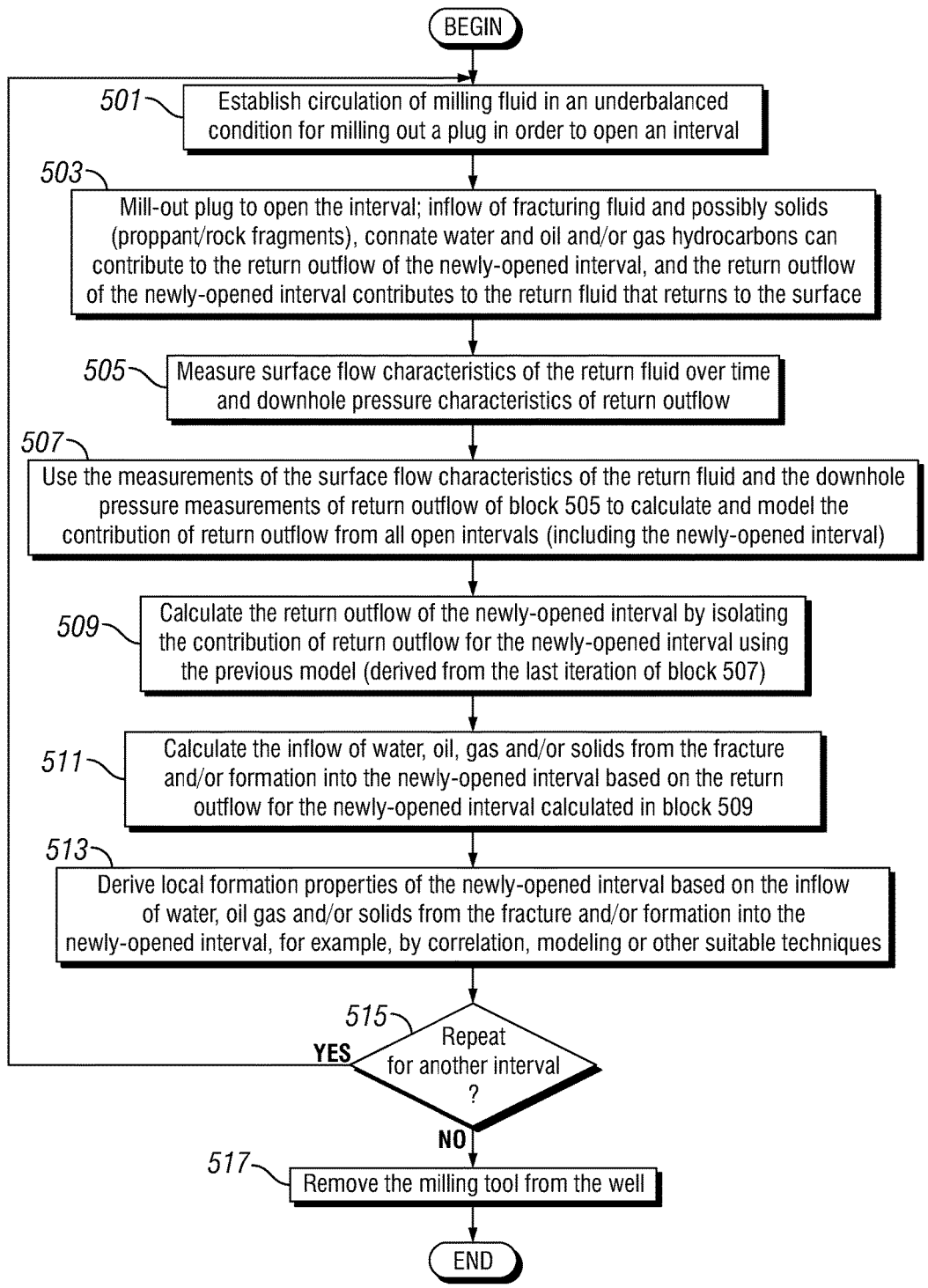
FIG. 5B is a flowchart illustrating exemplary operations carried out by the data analyzer of FIG. 2 that uses the fluid model of FIG. 5A to analyze the flow characteristics of return fluid during plug mill-out operations for the underbalanced condition in order to characterize local properties of the formation adjacent the newly-opened well interval.

FIG. 5B illustrates a workflow carried out by the data analyzer 207 of FIG. 2 that uses the fluid model of FIG. 5A to analyze the flow characteristics of return fluid during plug mill-out operations for the underbalanced condition in order to characterize local properties of the formation adjacent the newly-opened well interval. The workflow begins in block 501 where the supply of milling fluid in an underbalanced condition is established to power and lubricate the milling tool BHA 122 for milling out a plug in order to open a well interval. In block 503, the milling tool BHA 122 is operated to mill-out the plug to open the interval. In this case, the inflow of water (including water-based fracturing fluid and/or connate water) and possibly solids (proppant/rock fragments) and hydrocarbons (oil and gas) can contribute to the return outflow of the newly-opened interval, and the return outflow of the newly-opened interval contributes to the return fluid 130 that returns to the surface. In block 505, with the milling tool BHA 122 located in the newly-opened interval and the return outflow from the newly-opened interval contributing to the return fluid 130 at the surface, the data analyzer 207 can measure surface flow characteristics of the return fluid 130 over time and downhole pressure characteristics of the return outflow for the newly-opened interval. In block 507, the data analyzer 207 uses the measurements of the surface flow characteristics of the return fluid 130 and the downhole pressure measurements of return outflow of block 505 to calculate and model the return outflow from all open intervals (including the newly-opened interval) that is part of the return fluid 130 that returns to the surface. Note that the model of block 507 is a combination or convolution of the return outflow from all open intervals (including the newly-opened interval) of the well, and these open intervals are different over the sequence of well intervals that are opened by the plug mill-out operations. In block 509, the data analyzer 207 calculates the return outflow of the newly-opened interval by isolating the contribution of return outflow for the newly-opened interval from the previous model (derived from the last iteration of block 507). The calculations of block 509 can involve subtracting the return outflow from the previous model (derived from the last iteration of block 507) from the return outflow of the model derived in block 507. In block 511, the data analyzer 207 calculates the inflow of water, oil, gas and/or solids from the fracture and/or formation into the newly-opened interval based on the return outflow for the newly-opened interval calculated in block 509. In block 513, the data analyzer 207 derives local formation properties of the newly-opened interval based on the inflow of water, oil, gas and/or solids from the fracture and/or formation into the newly-opened interval as calculated in block 511, for example, by correlation, modeling or other suitable techniques. In block 515, it is determined whether the plug mill-out and corresponding data analysis operations of blocks 501 to 513 should be repeated to open and characterize another interval of the well. The determination of block 515 can be performed in an automated manner by computer evaluation of one or more predefined conditions, in a manual manner by human analysis of the data or in a semi-automated manner involving both computer evaluation and human analysis. If so, the workflow continues to block 501 to repeat blocks 501 to 513 for another interval. Otherwise, the milling tool BHA 122 can be removed from the well in block 517 and the workflow ends.

Note that as each plug is milled out, the new measurements of surface flow characteristics and downhole pressure measurements are used to update the calculations and model of block 507. Changes to the model between before and after the mill-out of each plug are then be used to isolate the contribution of return outflow for the newly-opened interval in block 509 and derive the inflow of water, oil, gas and/or solids from the fracture and/or formation into the newly-opened interval in block 511 and local formation properties based thereon in block 513. The sequence of well intervals that are opened by plug mill-out operations according to the workflow of FIG. 5B can be varied as desired. For example, the plugs can be milled out and corresponding intervals opened and characterized interval-by-interval from the heel to the toe of the well (or from the toe to the heel of the well).

In yet another embodiment, the data analyzer 207 can process the pressure measurements carried out by the downhole pressure sensor(s) 209 during the mill-out of a particular plug in order to identify pressure transients that indicate that the hydraulic isolation provide by the particular plug has been removed (in other words, the corresponding interval has been newly opened). The detection of such pressure transients together with the effective length and corresponding volume of the well to the newly-opened interval and the flow rate measurements of the surface-located multiphase flow meter 203 over time can be processed to identify the time interval for sampling and processing the flow rate measurements output by the surface-located multiphase flow meter 203 for characterizing the interval-specific flow contributions (such as the return outflow of milling fluid into the formation adjacent the newly-opened for the overbalanced condition or the inflow of water, oil, gas and/or solids into the newly-opened interval for the underbalanced condition). Furthermore, the transient decrease in circulating rate related to flow leak off in the newly-opened interval combined with the bottomhole pressure drop related to the reduction of friction pressure drop generated by the flow circulation can be used to quantify the size and conductivity of the fracture volume for the newly-opened interval. In the case of a fracture that has lost its connectivity with the wellbore, very little fluid will leak-off and the newly opened wellbore volume will pressure-up rapidly to the circulation pressure. For a large and conductive fracture well connected to the wellbore, the drop in flow rate related to fluid leaking off into the fractures of the newly-opened interval can provide an indication of good stimulation. The point at which the circulation pressure stabilizes can provide an indication of fluid leak-off from the fracture into the formation.

The measurements of surface flow characteristics and downhole pressure that are analyzed by the data analyzer 207 as described above can be performed under steady-state conditions where there are no surface-controlled variations in well pressure.

In another embodiment, the measurements of surface flow characteristics and downhole pressure that are analyzed by the data analyzer 207 as described above can be performed under dynamic transient conditions where there are surface-controlled variations in well pressure. In this case, the data analyzer 207 can interface to a well-head choke 201 via suitable data communication links (such as a wired electrical communication link, wireless RF communication link, or optical communication link) in order to communicate a choke control signal 211 that controls the operation of the choke 201. The choke 201 may include a variable sized aperture or orifice that is used to control fluid flow rate or downstream system pressure. As an example, the choke 201 may be provided in any of a variety of configurations (e.g., for fixed and/or adjustable modes of operation). As an example, an adjustable choke 201 may enable fluid flow and pressure parameters to be changed to suit process or production requirements. The choke 201 may be electrically or pneumatically operated. The data analyzer 207 can be configured to control the operation of the choke 201 (e.g., vary the aperture size of the choke) while the multiphase flow meter 203 performs the multiphase flow rate measurements on the return fluid 130 during the mill-out operations. The controlled operation of the choke 201 (e.g., controlled variation in the aperture size of the choke) can be configured to create transient variations or perturbations in downhole pressure in a newly-opened interval (i.e., after the corresponding plug that has been milled out). These transient pressure perturbations can be used as part of the nodal analysis and modeling of the data analyzer 207 that determines the flow contribution of water, oil, gas, and/or solids from the formation into the newly-opened interval as well as the effective open wellbore length that characterizes the newly-opened interval. More specifically, as wellhead pressure is increased or decreased by operation of the choke 201 a surge or drop in bottomhole pressure will lead to an increase or decrease in injection into the formation (in the case of overbalance flow). In an underbalance scenario, the surge or drop in bottomhole pressure will lead to a decrease or increase in the inflow of water, oil, gas and/or solids from the formation. This modification in flow behavior will be a function of the fracture network size, conductivity and connectivity with the wellbore as well as a function of the formation response for the newly-opened interval. A monitoring of the bottomhole pressure can allow an engineer to manually identify (or can allow the data analyzer 207 itself to automatically identify) which model used by the data analyzer 207 best fits the pressure response for each interval.

In one or more embodiments, the milling fluid can include a tracer compound (or multiple tracer compounds) that can help to quantitatively distinguish the milling fluid from one or more produced fluid phases, such as a water phase (including fracturing fluid and/or connate water), an oil hydrocarbon phase and/or a gas hydrocarbon phase. In one example, the tracer compound can be an iodide salt, a high solubility dye or other suitable compound that is readily distinguishable from the formation fluids (e.g., connate water, oil and gas hydrocarbons) and the fracturing fluids used to fracture the formation. The tracer compound(s) can be added to the milling fluid continuously or in pulses. The concentration of the tracer compound(s) can be varied in a controlled manner in conjunction with controlled pressure variations of the milling fluid supplied to the milling bit during plug mill-out operations in order to discriminate between sources and sinks of reservoir fluids during the plug mill-out operations. As shown in FIG. 2, the surface facility can also include a chemical analyzer 211 that analyzes the return fluid 130 to obtain quantitative information (e.g., concentration) of the tracer compound(s) in the return fluid 130 over time.

Figure 6:
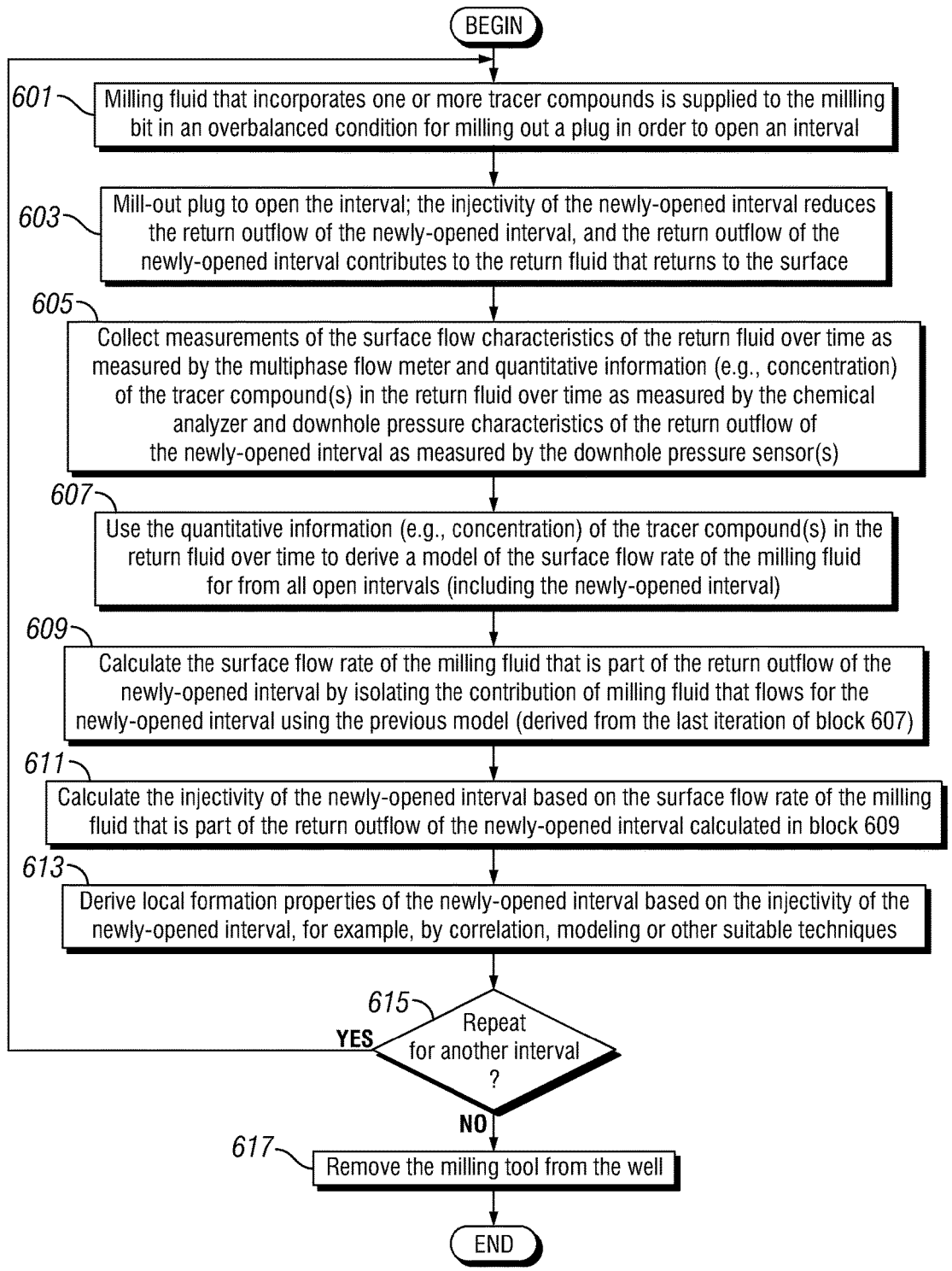
FIG. 6 is a flowchart illustrating exemplary operations carried out by the data analyzer of FIG. 2 that uses milling fluid that incorporates one or more tracer compounds as well as the fluid model of FIG. 4A to analyze the flow characteristics of return fluid during plug mill-out operations for the overbalanced condition in order to characterize local properties of the formation adjacent the newly-opened well interval.

In the overbalanced condition of the milling fluid as shown in the workflow of FIG. 6, the operations begin in block 601 where milling fluid that incorporates one or more tracer compounds is supplied in an overbalanced condition to power and lubricate the milling tool BHA 122 for milling out a plug in order to open a well interval. In block 603, the milling tool BHA 122 is operated to mill-out the plug to open the interval. In this case, the injectivity of the newly-opened interval reduces the return outflow of the newly-opened interval, and the return outflow of the newly-opened interval contributes to the return fluid 130 that returns to the surface. In block 605, with the milling tool BHA 122 located in the newly-opened interval and the return outflow from the newly-opened interval contributing to the return fluid 130 at the surface, the data analyzer 207 can collect measurements of the surface flow characteristics of the return fluid 130 over time as measured by the multiphase flow meter 203 and quantitative information (e.g., concentration) of the tracer compound(s) in the return fluid 130 over time as measured by the chemical analyzer 211 and downhole pressure characteristics of the return outflow of the newly-opened interval as measured by the downhole pressure sensor(s) 209. In blocks 607 to 611, the data analyzer 207 can evaluate the quantitative information (e.g., concentration) of the tracer compound(s) in the return fluid 130 over time as measured by the chemical analyzer 211 in order to determine the injectivity (leakoff) of the milling fluid for the newly-opened interval. Specifically, in block 607, the data analyzer 207 can use quantitative information (e.g., concentration) of the tracer compound(s) in the return fluid 130 over time to derive a model of the surface flow rate of the milling fluid (which flows as part of the return fluid 130) for all open intervals (including the newly-opened interval). Note that the model of block 607 is a combination or convolution of the milling fluid that is part of the return outflow from all open intervals (including the newly-opened interval) of the well, and these open intervals are different over the sequence of well intervals that are opened by the plug mill-out operations. In block 609, the data analyzer 207 calculates the surface flow rate of the milling fluid that is part of the return outflow of the newly-opened interval by isolating the contribution of milling fluid for the newly-opened interval from the previous model (derived from the last iteration of block 607). The calculations of block 609 can involve subtracting the milling fluid flow rate from the previous model (derived from the last iteration of block 607) from the milling fluid flow rate model derived in block 607. In block 611, the data analyzer 207 can calculate the injectivity of the newly-opened interval based on the surface flow rate of the milling fluid that is part of the return outflow of the newly-opened interval calculated in block 609. In block 613, the data analyzer 207 can derive local formation properties of the newly-opened interval based on the injectivity (leakoff) of the milling fluid into the fracture and/or formation of the newly-opened interval as calculated in block 609, for example, by correlation, modeling or other suitable techniques. In block 615, it is determined whether the plug mill-out and corresponding data analysis operations of blocks 601 to 613 should be repeated to open and characterize another interval of the well. The determination of block 615 can be performed in an automated manner by computer evaluation of one or more predefined conditions, in a manual manner by human analysis of the data or in a semi-automated manner involving both computer evaluation and human analysis. If so, the workflow continues to block 601 to repeat blocks 601 to 613 for another interval of the well. Otherwise, the milling tool BHA 122 can be removed from the well in block 617 and the workflow ends.

Figure 7A:
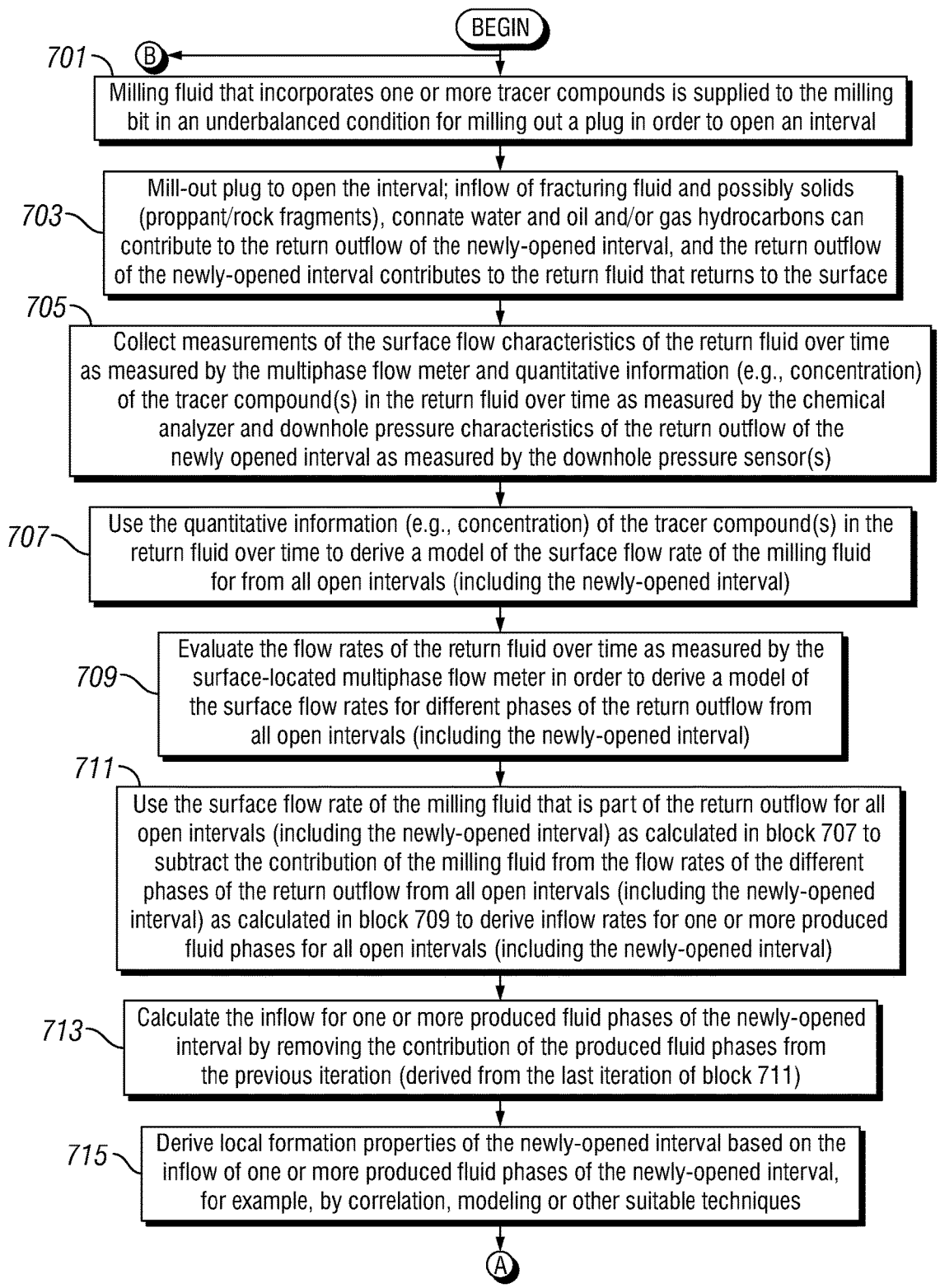
FIGS. 7A and 7B, collectively, is a flowchart illustrating exemplary operations carried out by the data analyzer of FIG. 2 that uses milling fluid that incorporates one or more tracer compounds as well as the fluid model of FIG. 5A to analyze the flow characteristics of return fluid during plug mill-out operations for the underbalanced condition in order to characterize local properties of the formation adjacent the newly-opened well interval.
Figure 7B:
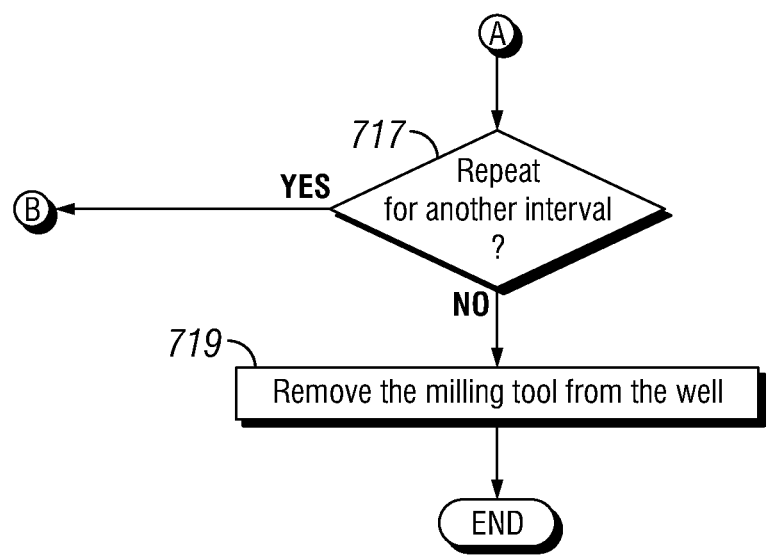

In the underbalanced condition of the milling fluid as shown in the workflow of FIGS. 7A and 7B, the operations begin in block 701 where milling fluid that incorporates one or more tracer compounds is supplied in an underbalanced condition to power and lubricate the milling tool BHA 122 for milling out a plug in order to open a well interval. In block 703, the milling tool BHA 122 is operated to mill-out the plug to open the interval. In this case, inflow of fracturing fluid and possibly solids (proppant/rock fragments), connate water and oil and/or gas hydrocarbons can contribute to the return outflow of the newly-opened interval, and the return outflow of the newly-opened interval contributes to the return fluid that returns to the surface. In block 705, with the milling tool BHA 122 located in the newly-opened interval and the return outflow from the newly-opened interval contributing to the return fluid 130 at the surface, the data analyzer 207 can collect measurements of the surface flow characteristics of the return fluid 130 over time as measured by the multiphase flow meter 203 and quantitative information (e.g., concentration) of the tracer compound(s) in the return fluid 130 over time as measured by the chemical analyzer 211 and downhole pressure characteristics of the return outflow of the newly-opened interval as measured by the downhole pressure sensor(s) 209. In blocks 707 to 713, the data analyzer 207 can evaluate the quantitative information (e.g., concentration) of the tracer compound(s) in the return fluid 130 over time as measured by the chemical analyzer 211 in order to determine the inflow of one or more produced fluid phases (such as produced water including water-based fracturing fluid and possibly connate water, oil hydrocarbons and/or gas hydrocarbons) that flow from the formation and fractures into the newly-opened interval. Specifically, in block 707, the data analyzer 207 can evaluate the quantitative information (e.g., concentration) of the tracer compound(s) in the return fluid 130 over time as measured by the chemical analyzer 211 to derive a model of the surface flow rate of the milling fluid (which flows as part of the return fluid 130) for all open intervals (including the newly-opened interval). Note that the model of block 707 is a combination or convolution of the milling fluid that is part of the return outflow from all open intervals (including the newly-opened interval) of the well, and these open intervals are different over the sequence of well intervals that are opened by the plug mill-out operations. In block 709, the data analyzer 207 can also evaluate the flow rates of the return fluid 130 over time as measured by the surface-located multiphase flow meter 203 in order to derive a model of the surface flow rates for different phases of the return outflow from all open intervals (including the newly-opened interval) of the well, and these open intervals are different over the sequence of well intervals that are opened by the plug mill-out operations. In block 711, the data analyzer 207 can use the surface flow rate of the milling fluid that is part of the return outflow for all open intervals (including the newly-opened interval) as calculated in block 707 to subtract the contribution of the milling fluid from the flow rates of the different phases of the return outflow from all open intervals (including the newly-opened interval) as calculated in block 709 to derive inflow rates for one or more produced fluid phases for all open intervals (including the newly-opened interval) of the well. For example, in the case involving water-based milling fluid with one or more tracer compounds, the data analyzer 207 can use the surface flow rate of the water-based milling fluid calculated in block 709 to subtract the contribution of the water-based milling fluid from all open intervals (including the newly-opened interval) of the well from the flow rate for the water phase for all open intervals (including the newly-opened interval) as calculated in block 709 to derive flow rates for one or more produced fluid phases for all open intervals (including the newly-opened interval) of the well. In block 713, the data analyzer 207 calculates the inflow for one or more produced fluid phases of the newly-opened interval by removing the contribution of the produced fluid phases from the previous iteration (derived from the last iteration of block 711). The calculations of block 713 can involve subtracting the inflow for one or more produced fluids from the previous iteration (derived from the last iteration of block 711) from the corresponding inflow for the one or more produced fluid derived in block 711. In block 715, the data analyzer 207 can derive local formation properties of the newly-opened interval based on the inflow of one or more produced fluid phases from the fracture and/or formation into the newly-opened interval as calculated in block 713, for example, by correlation, modeling or other suitable techniques. In block 717, it is determined whether the plug mill-out and corresponding data analysis operations of blocks 701 to 715 should be repeated to open and characterize another interval of the well. The determination of block 717 can be performed in an automated manner by computer evaluation of one or more predefined conditions, in a manual manner by human analysis of the data or in a semi-automated manner involving both computer evaluation and human analysis. If so, the workflow continues to block 701 to repeat blocks 701 to 715 for another interval of the well. Otherwise, the milling tool BHA 122 can be removed from the well in block 719 and the workflow ends.

Figure 8A:
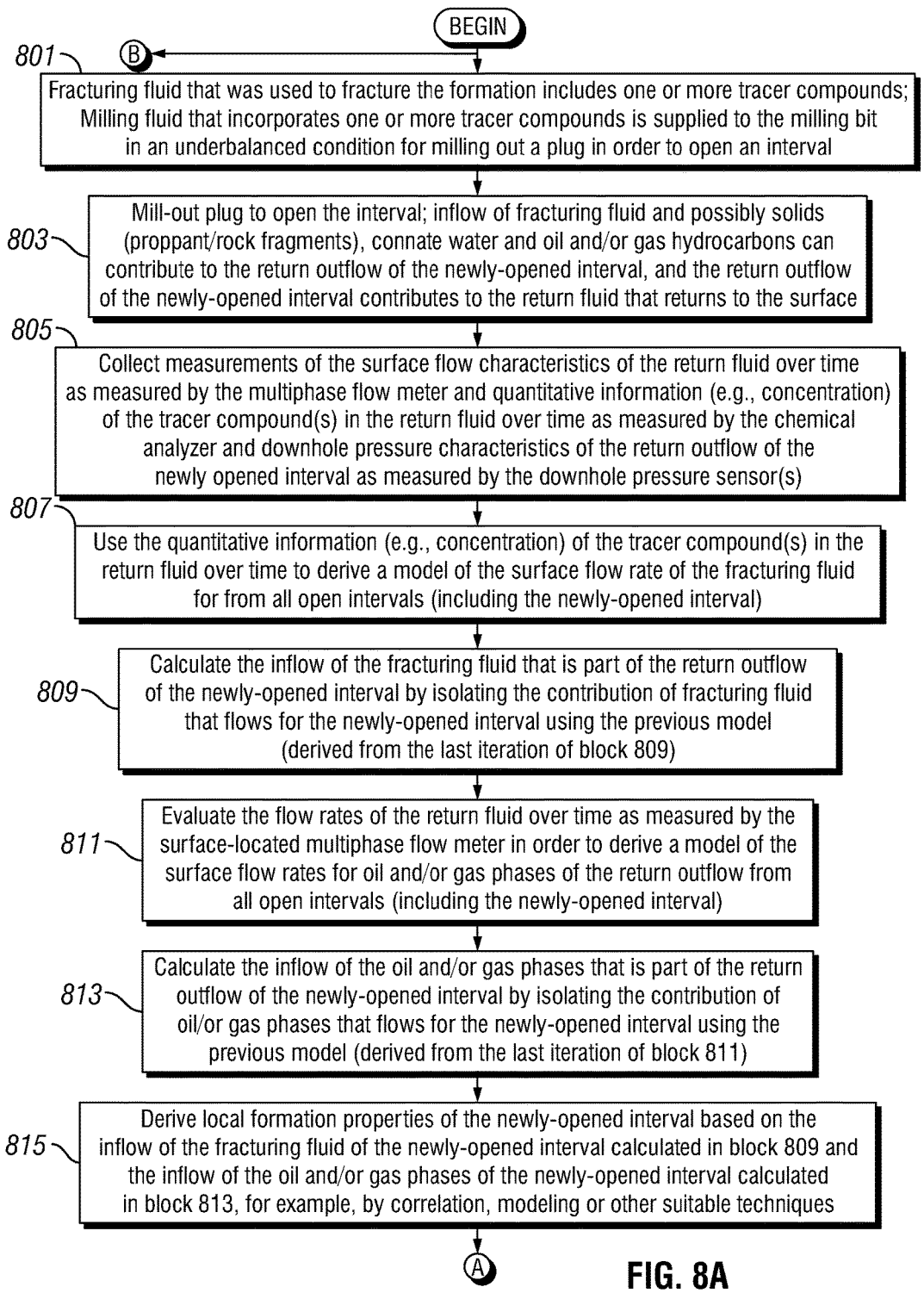
FIGS. 8A and 8B, collectively, is a flowchart illustrating exemplary operations carried out by the data analyzer of FIG. 2 that uses fracturing fluid that incorporates one or more tracer compounds as well as the fluid model of FIG. 5A to analyze the flow characteristics of return fluid during plug mill-out operations for the underbalanced condition in order to characterize local properties of the formation adjacent the newly-opened well interval.
Figure 8B:
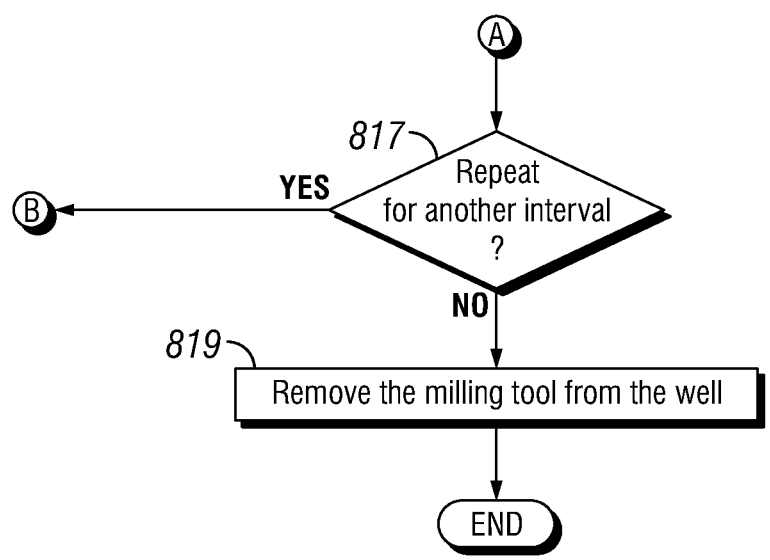

In one or more embodiments, the fracturing fluid that is used to fracture the formation can include a tracer compound (or multiple tracer compounds) that can help to quantitatively distinguish the fracturing fluid from the milling fluid and/or other produced fluids (such as connate water). In one example, the tracer compound can be an iodide salt, a high solubility dye or other suitable compound that is readily distinguishable from the formation fluids (e.g., connate water, oil and gas hydrocarbons) and the milling fluid used to mill-out the plugs. The surface facility can also include a chemical analyzer 211 that analyzes the return fluid 130 to obtain quantitative information of the tracer compound(s) in the return fluid 130. In the underbalanced condition of the milling fluid as shown in the workflow of FIGS. 8A and 8B, the operations begin in block 801 where the fracturing fluid that was used to fracture the formation includes one or more tracer compounds, and milling fluid is supplied in an underbalanced condition to power and lubricate the milling tool BHA 122 for milling out a plug in order to open a well interval. In block 803, the milling tool BHA 122 is operated to mill-out the plug to open the interval. In this case, inflow of fracturing fluid and possibly solids (proppant/rock fragments), connate water and oil and/or gas hydrocarbons can contribute to the return outflow of the newly-opened interval, and the return outflow of the newly-opened interval contributes to the return fluid that returns to the surface. In block 805, with the milling tool BHA 122 located in the newly-opened interval and the return outflow from the newly-opened interval contributing to the return fluid 130 at the surface, the data analyzer 207 can collect measurements of the surface flow characteristics of the return fluid 130 over time as measured by the multiphase flow meter 203 and quantitative information (e.g., concentration) of the tracer compound(s) in the return fluid 130 over time as measured by the chemical analyzer 211 and downhole pressure characteristics of the return outflow of the newly-opened interval as measured by the downhole pressure sensor(s) 209. In blocks 807 to 813, the data analyzer 207 can evaluate the quantitative information (e.g., concentration) of the tracer compound(s) in the return fluid 130 over time as measured by the chemical analyzer 211 in order to determine the inflow of the fracturing fluid that flows from the formation and fractures into the newly-opened interval. Specifically, in block 807, the data analyzer 207 can evaluate the quantitative information (e.g., concentration) of the tracer compound(s) in the return fluid 130 over time as measured by the chemical analyzer 211 to derive a model of the surface flow rate of the fracturing fluid (which flows as part of the return fluid 130) for all open intervals (including the newly-opened interval). Note that the model of block 807 is a combination or convolution of the fracturing fluid that is part of the return outflow from all open intervals (including the newly-opened interval) of the well, and these open intervals are different over the sequence of well intervals that are opened by the plug mill-out operations. In block 809, the data analyzer 207 can calculate the inflow of fracturing fluid for the newly-opened interval by removing the contribution of the fracturing fluid from the previous iteration (derived from the last iteration of block 807). The calculations of block 809 can involve subtracting the inflow of the fracturing fluid from the previous iteration (derived from the last iteration of block 807) from the corresponding inflow of fracturing fluid derived in block 807. In block 811, the data analyzer 207 can also evaluate the flow rates of the return fluid 130 over time as measured by the surface-located multiphase flow meter 203 in order to derive a model of the surface flow rates for oil and/or gas phases of the return outflow from all open intervals (including the newly-opened interval) of the well, and these open intervals are different over the sequence of well intervals that are opened by the plug mill-out operations. In block 813, the data analyzer 207 can calculate the inflow of oil and/or gas for the newly-opened interval by removing the contribution of the oil and/or gas from the previous iteration (derived from the last iteration of block 811). The calculations of block 813 can involve subtracting the inflow of oil and/or gas from the previous iteration (derived from the last iteration of block 811) from the corresponding inflow of oil and/or gas derived in block 811. In block 815, the data analyzer 207 can derive local formation properties of the newly-opened interval based on the inflow of the fracturing fluid of the newly-opened interval calculated in block 809 and the inflow of the oil and/or gas phases of the newly-opened interval calculated in block 813, for example, by correlation, modeling or other suitable techniques. In block 817, it is determined whether the plug mill-out and corresponding data analysis operations of blocks 801 to 815 should be repeated to open and characterize another interval of the well. The determination of block 817 can be performed in an automated manner by computer evaluation of one or more predefined conditions, in a manual manner by human analysis of the data or in a semi-automated manner involving both computer evaluation and human analysis. If so, the workflow continues to block 801 to repeat blocks 801 to 815 for another interval of the well. Otherwise, the milling tool BHA 122 can be removed from the well in block 819 and the workflow ends.

In one or more embodiment, the data analysis performed by the data analyzer 207 can incorporate wellhead and/or downhole pressure survey(s) during the plug mill-out operation to increase the sensitivity of identifying and locating sources and sinks of milling fluid, residual fracturing fluids and formation fluids for the respective intervals of the well.

In one or more embodiments, the surface facility can include a gas analyzer 213 as shown in FIG. 2. The gas analyzer extracts and quantitatively analyzes hydrocarbon gas entrained in the return fluid 130 over time as the return fluid 130 flows to the surface during the plug mill-out operations. Hydrocarbon gases can enter the return fluid 130 by flow from the formation to the wellbore (depending on the difference between the formation pressure and the wellbore pressure). The gas analysis system can operate by extracting hydrocarbon gases from the return fluid 130 and then analyzing those hydrocarbon gases. Extraction can be performed using an extractor or a degasser such as the FLEX™ fluid extractor commercially available from Schlumberger Technology Corporation of Sugar Land, Tex. that continuously samples the return fluid 130 that returns from the well and heats the return fluid samples to a constant temperature under constant pressure and volume conditions for extraction of hydrocarbon gases. The extracted hydrocarbon gases can be analyzed by a gas chromatograph or a gas chromatograph/mass spectrometer in order to obtain a quantitative evaluation of the extracted hydrocarbon gases. Such analysis can obtain a quantitative evaluation of light gases $C_1$ through $C_5$ and information on heavier hydrocarbon components (such as $C_6$ to $C_8$ including methylcyclohexane and the light aromatics benzene and toluene) and nonhydrocarbon components (such as helium, hydrogen, carbon dioxide and hydrogen sulfide). For example, such analysis can involve the FLAIR™ system which is commercially available from Schlumberger Technology Corporation of Sugar Land, Tex. Such analysis can also involve isotope measurements which are commercially available from Schlumberger Technology Corporation of Sugar Land, Tex. Analysis can also use tandem mass spectrometry as described in U.S. Pat. No. 8,536,524, entitled, "Fast Mud Gas Logging using Tandem Mass Spectroscopy," and incorporated by reference herein in its entirety. The concentration of hydrocarbon gases entering the well due to recirculation of milling fluid can be subtracted from the concentration of hydrocarbon gases exiting the well to correct for gas recycling. The quantitative evaluation (e.g., concentration) of the extracted hydrocarbon gases (e.g., concentration) measured by the gas analysis system over time can be used as part of the surface flow rate measurements described herein to quantify the inflow of hydrocarbon gases from the respective well intervals during the plug mill-out operations. The data analyzer can derive local formation properties of the respective well interval based on the inflow of the hydrocarbon gases (possibly together with the inflow other formation fluids, such as connate water, and fracturing fluids or other flowback fluids) that flow from, the fractures and/or formation of the newly-opened interval into the wellbore, for example, by correlation, modeling or other suitable techniques.

In one or more embodiments, the surface facility can employ measurements where certain fluid elements (slugs) of the milling fluid that is pumped downhole for supply to the milling bit are tagged. In one example, a tracer compound (or multiple tracer compounds) can be incorporated into the milling fluid such that tracer compound(s) tags the respective milling fluid slug. In another example, a pulsed neutron source can tag the respective milling fluid slug with a neutron radiation such that the respective milling fluid slug emits gamma ray radiation. One or more fluid properties of the respective milling fluid slugs that are pumped downhole for supply to the milling bit are also measured. For example, a surface-located gas analysis system can extract and quantitatively analyze the concentration of hydrocarbon gas entrained in the respective milling fluid slugs that are pumped downhole for supply to the milling bit. The circulation of the milling fluid causes the respective tagged milling fluid slugs to return to the surface facility as part of the return fluid 130. A surface-located detector, for example a chemical analyzer that detects the tracer compound(s) or one or more gamma ray detectors, can be configured to detect the respective tagged milling fluid slugs at the surface. One or more fluid properties of the respective tagged milling fluid slugs are also measured. For example, the surface-located gas analysis system can extract and quantitatively analyze the concentration of hydrocarbon gas entrained in the respective tagged milling fluid slugs that return to the surface facility. The difference between the properties of the tagged milling fluid slugs from supply to return can be used to characterize the injectivity (leakoff) or inflow from one well interval from the injectivity (leakoff) or inflow from the other well intervals and thus to characterize the local formation properties of the one well interval based on the injectivity (leakoff) or inflow from one well interval.

In one or more embodiments, the pumping rate of the milling fluid can be controlled such that the return rate of the return fluid is maintained within a range that is intended to maintain substantial stability of proppant pack in the fractures of the opened interval(s) of the well during the plug drill-out operations or enables control over proppant flowback from the fractures of the opened interval(s) of the well during the plug drill-out operations.

In other embodiments, the method and system can analyze flow characteristics of return fluid that flows to a surface-located facility during well cleanout or workover operations. In this case, cleanout or workover fluid (which is analogous to the milling fluid as described above) can be pumped to a downhole tool for cleanout or workover of the wellbore. The cleanout or workover fluid can incorporate one or more tracer compounds as described herein. Local formation properties can be determined based upon the flow characteristics of the return fluid during the well cleanout or workover operations in a manner similar to the plug mill-out operations as described herein.

Figure 9:
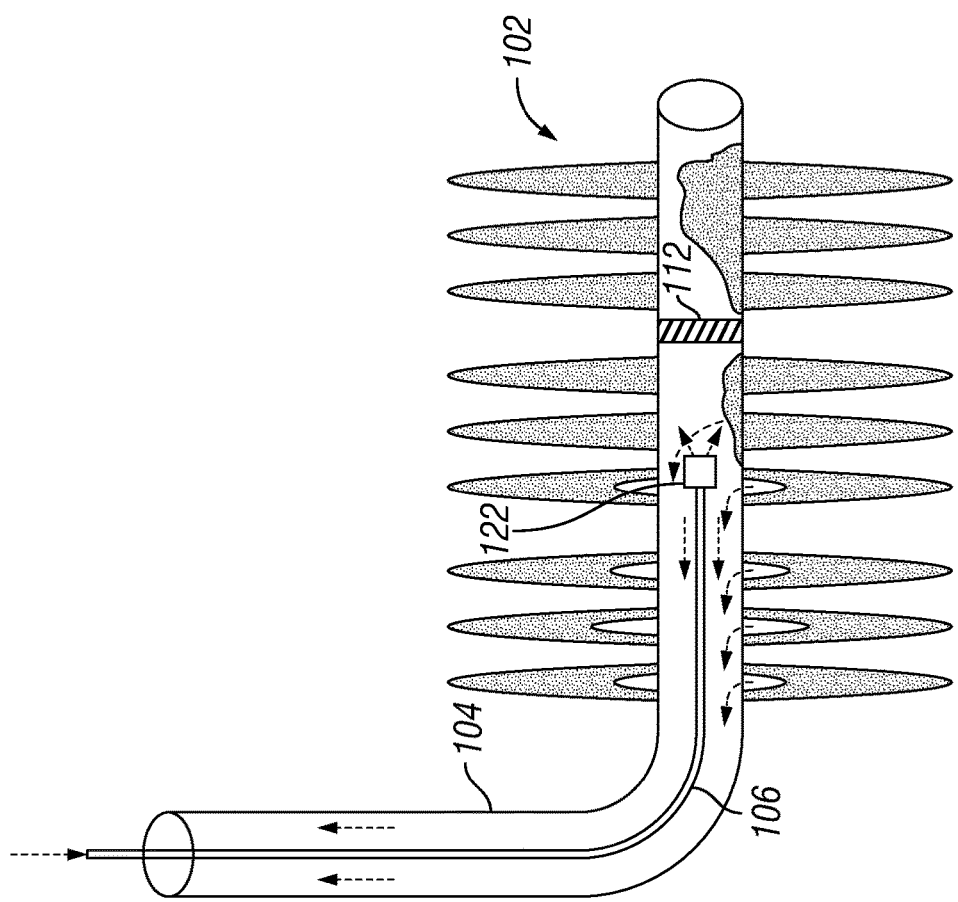
FIG. 9 is a schematic illustration of a well that traverses a hydraulically-fractured hydrocarbon-bearing reservoir. The well includes a horizontal section with production tubing that includes a number of perforation zones that are offset from one another along the length of the horizontal section of the well. A BHA can be run in the well for performing plug mill-out and clean-out operations (and possibly other operations) on the well.

In one embodiment shown in FIG. 9, the BHA 122 as described herein can be moved along the sequence of intervals of the well to mill-out the plugs (one shown as bridge plug 112) that isolate the intervals of the well, for example from the heel to the toe of the well. After milling out a plug, the BHA 122 can be used to supply fluid to the wellbore of the newly-opened well interval in order to clean out the interval. Specifically, sand, proppant, rock fragments and/or other solid debris can be deposited in the wellbore of the interval prior to the mill-out and clean out workflow. The supplied fluid can mobilize such solids, and the mobilized solids can be carried in the return fluid that returns to the surface as shown. The return fluid can also carry solids (e.g., sand, proppants, and rock fragments) that are produced from the fractures (and possibly the adjacent formation) in fluid communication with the perforated zones of the opened intervals that are upstream and possibly downstream of the BHA 122 as shown. As part of this workflow, one or more parameters that characterize solids production over the opened intervals and associated perforated zones of the well can be calculated as the BHA 122 is moved along the sequence of intervals during the workflow that mill-outs the plugs and cleans out the intervals of the well. The one or more parameters that characterize solids production of the intervals and associated perforated zones of the well can be used to dynamically control the operations and/or plan the next treatment of the well to reduces solids production of the well (if need be) and/or plan production strategies for the well that reduces solids production of the well (if need be).

Figure 10:
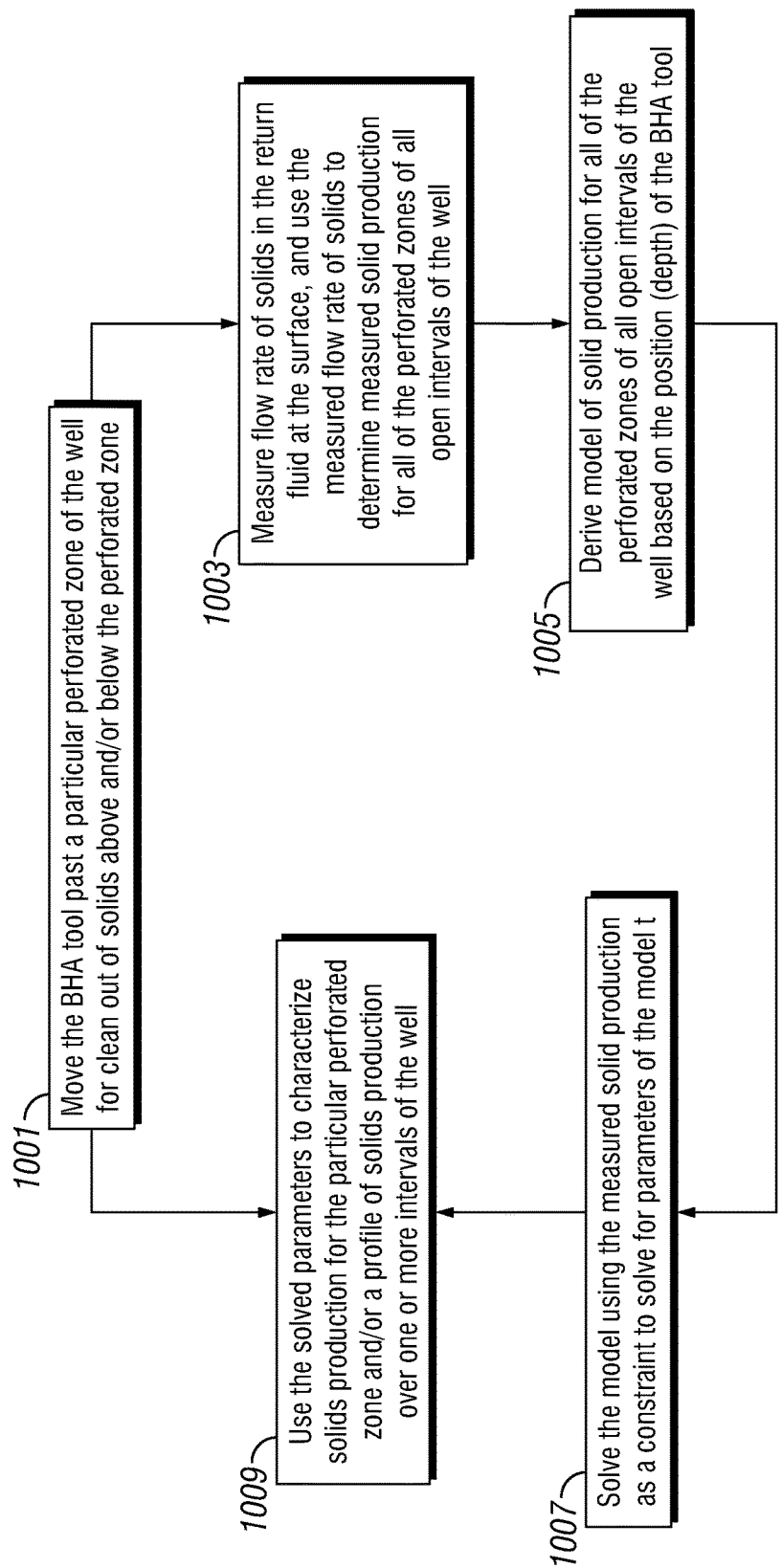
FIG. 10 is a flowchart illustrating operations carried out by the data analyzer of FIG. 2 that measures the inflow of produce solids corresponding to the location of the BHA and characterizes solids production associated with one or more perforated zones of the well.

FIG. 10 illustrates a workflow carried out by the data analyzer 207 of FIG. 2 to analyze the flow characteristics of return fluid during clean out operations that can be performed in conjunction with plug mill-out operations over the intervals of a well. The workflow begins in block 1001 where the BHA 122 is moved past a particular perforated zone of the well with the supply of fluid to the BHA 122 established for clean out of solids above and/or below the particular perforated zone. In this block 1001, the supplied fluid can mobilize solids near the particular perforated zone, and the mobilized solids can be carried in the return fluid that returns to the surface. The return fluid can also carry solids that are produced from the fractures (and possibly the adjacent formation) that are in fluid communication with the perforated zones of the opened interval(s) upstream and possibly downstream the BHA tool position. In block 1003, the data analyzer 207 can measure surface low rate of solids that are part of return fluid over time and use the measure flow rate of solids to determine measured solid production for all of the perforated zones of all open intervals of the well as a function of the location of the BHA 122. The data analyzer 207 can optionally use downhole pressure measurements to correct measured flow rates in order to account for leakoff of the supplied fluid into the fractures and/or formation. In block 1005, the data analyzer 207 derives a model of solids production for all of the perforated zones for all open intervals of the well based on position (depth) of the BHA 122 in the well. In block 1007, the data analyzer 207 solves the model of solids production as derived in the block 1005 for the current location of the BHA 122 using the measured solid production as determined in block 1003 for the current location of the BHA 122 as a constraint to solve for parameters of the model. In block 1009, the data analyzer 207 can employ the parameters solved in block 1007 to derive parameters that character solids production for the particular perforated zone, such as volume of solids produced from fractures and/or formation in fluid communication with the particular perforated zone.

Note that the operations of blocks 1001 to 1009 can be performed iteratively over a sequence of perforated zones for intervals that are opened by the plug mill-out operations in order to derive the parameters that character solids production over the perforated zones. For example, these parameters can be combined to determine a profile of solids production over the sequence of perforated zones of the well. For example, the profile of solids production can include volume of solids produced from fractures and/or formation over well depths that encompass the sequence of perforated zones as a mass distribution of deposited solids over one or more intervals of the well. The sequence of well intervals and corresponding perforated zones that are opened and cleaned out can be varied as desired. For example, the well intervals and corresponding perforated zones can be opened and cleaned out from the heel to the toe of the well.

In one example where the BHA 122 supplies fluid to the wellbore of each newly-opened interval in an underbalanced condition (i.e., less than the formation pressure) for clean out of the newly-opened interval, the production of solids from fractures that are in communication with a perforated zone of the newly-opened interval can be described by an exponentially decreasing function of the form:

$$U_{sand} = A_i e^{-\alpha_i t} \qquad \text{Eqn. (1)}$$

where $U_{sand}$ is the rate of solids production (e.g., kg/min) from the i-th perforated zone of the well,
$A_i$ and $\alpha_i$ are coefficients of the exponentially decreasing function, and
t represents the time after the location of the BHA 122 passes the i-th perforated zone.

Note that Eqn. (1) can also describe the production of solids from fractures and/or formation that are in communication with a perforated zone of an open interval located above the position of the BHA.

We also assume that solids may be deposited in the wellbore next to each perforated zone (or between perforated zones or other locations), where such solids have a distribution described by an exponentially decreasing function of the form:

$$\overline{m}_{sand} = B_i e^{-\beta_i(x-x_i)^2} \quad \text{Eqn. (2)}$$

Where $\overline{m}_{sand}$ is the solid distribution (e.g., kg/m) along the wellbore,
$B_i$ and $\beta_i$ are coefficients of the exponentially decreasing function,
x is the location (depth) of the BHA, and
$x_i$ is the location (depth) of the sand deposit.

We can also assume that no solids production occurs from the perforated zones below the BHA tool, which is typically correct for slightly underbalanced types of clean out operations as well as balanced and overbalanced type of clean out operations.

Under these assumptions, a profile of solids concentration as the BHA 122 is moved along the perforated zones of the well can be described by the following parametric equation:

$$C_{solids} = \frac{1}{\text{pump rate}} \sum_{i=1}^{N} \left\{ \begin{array}{l} A_i e^{-\alpha_i \left[ \frac{x-y_i}{BHA_{Speed}} - \frac{(y_i-y_1)\times AVC}{\text{pump rate}} \right]}; \text{ if } x \geq y_i \text{ and} \\ \left[ \frac{x-y_i}{BHA_{Speed}} - \frac{(y_i-y_1)\times AVC}{\text{pump rate}} \right] \geq 0 \\ 0; \text{ if } x < y_i \text{ or } \left[ \frac{x-y_i}{BHA_{Speed}} - \frac{(y_i-y_1)\times AVC}{\text{pump rate}} \right] < 0 \end{array} \right\} + \frac{BHA_{speed}}{\text{pump rate}} \sum_{i=1}^{N} \left[ B_i e^{-\beta_i \left( \frac{x+y_1 \frac{BHA_{Speed} \times AVC}{\text{pump rate}}}{1+\frac{BHA_{Speed}\times AVC}{\text{pump rate}}} - x_i \right)^2} \right] \quad \text{Eqn. (3)}$$

where $C_{solids}$ is solids concentration (kg added to m3) for a given location (depth) x of the BHA as the BHA is moved along the perforated zones of the well,
$A_i$ and $\alpha_i$ are coefficients of the exponentially decreasing function of the first summation term,
$B_i$ and $\beta_i$ are coefficients of the exponentially decreasing function of the second summation term,
x is the location (depth) of the BHA,
$y_i$ is the location (depth) of i-th perforated zone,
$y_1$ is the location (depth) of the 1st perforated zone,
$x_i$ is the location (depth) of the sand deposit
pump rate (e.g., cubic meters/min) is the rate of supply of fluid to the BHA,
$BHA_{speed}$ is the speed of the BHA as it moves along the perforated zones of the well, and
AVC is the volume capacity (e.g., in cubic meters/m) of the annulus that carries the return fluid to the surface, which can be determined from the external diameter of the tubing that runs the BHA tool and the internal wellbore diameter/casing of the well.

In this Eqn. (3), the solids concentration $C_{solids}$ represents the contribution of solids from all of the perforated zones for all open intervals of the well. The first summation term is derived from the exponentially decreasing function of Eqn. (1) and represents the contribution of solids that are produced from the fractures and/or formation that are in fluid communication with the perforated zones for all open intervals of the well. The second summation term is derived from the exponentially decreasing function of Eqn. (2) and represents the contribution of deposited solids near (or between) the perforated zones for all open intervals of the well.

The parametric equation of Eqn. (3) can be used as the model of solid production of block 1005 for the workflow of FIG. 10. The measured solids concentration of block 1003 can be used as a constraint to find a best-fit solution to the parametric equation of Eqn. (3) as the BHA 122 is moved along the perforated zones of the well. The solution provides values for the coefficients $A_i$, $\alpha_i$, $B_i$, $\beta_i$, and $x_i$ of the parametric equation of Eqn. (3) for a sequence of perforated zones of the well. The solved-for values can be used to derive parameters that characterize the solids production from each perforated zone. In one example, these parameters can include a total volume of solids produced from the fractures of a given perforated zone, which can be calculated as:

$$V_{solids_i} = \frac{A_i}{\alpha_i}. \quad \text{Eqn. (4)}$$

The parameters $V_{solids_i}$ of Eqn. (4) for the sequence of perforated zones can be combined to determine a profile of solids production over the sequence of perforated zones of the well. For example, the profile of solids production can include the volume of solids produced from fractures and/or formation over well depths that encompass the sequence of perforated zones as derived from the parameters $V_{solids_i}$ for the sequence of perforated zones.

The parameters of the model can also provide a mass distribution of solids over one or more intervals of the well, which can be calculated as:

$$\overline{M}_{solids} = \sum_{i=1}^{N} B_i e^{-\beta_i(x-x_i)^2}. \quad \text{Eqn. (5)}$$

Figure 11A:
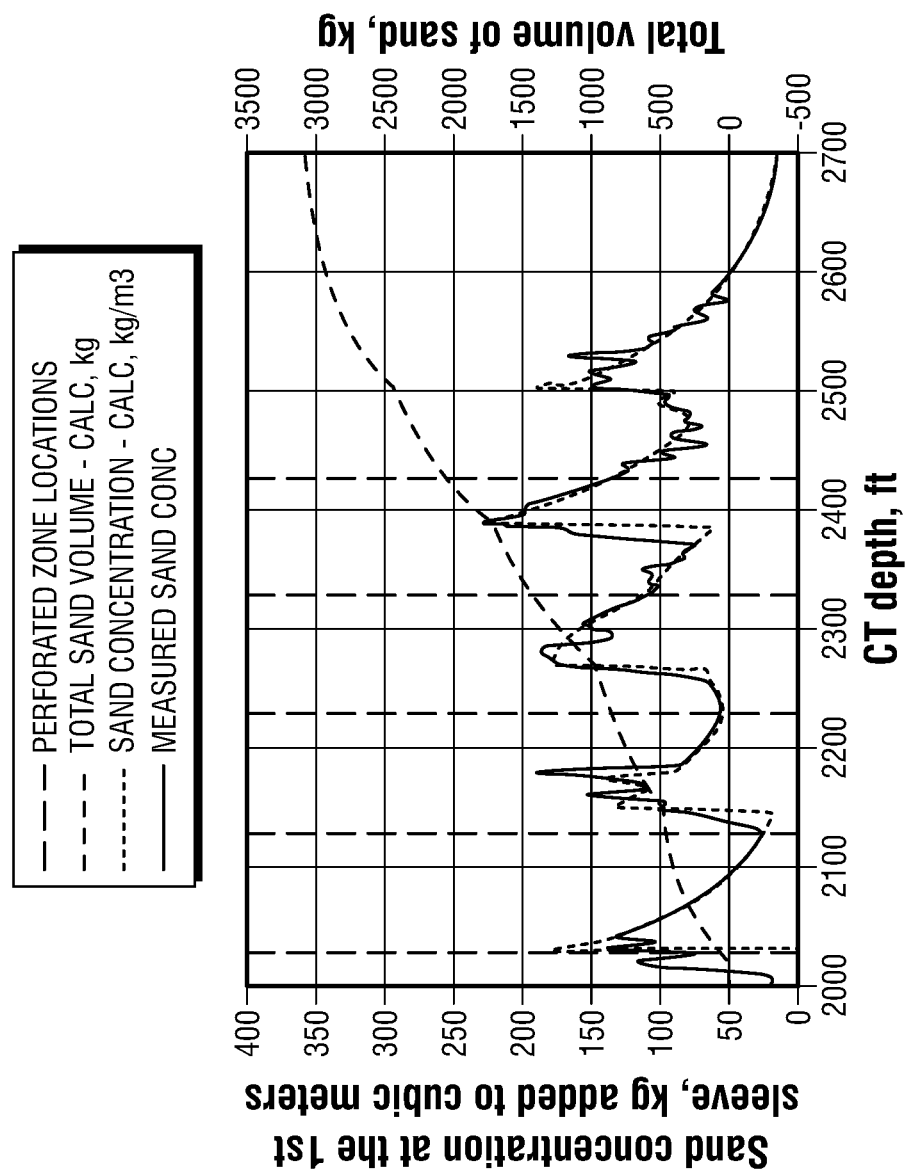
FIGS. 11A and 11B are plots that illustrate the data processing operations of the data analyzer during an exemplary slightly underbalanced clean out operation according to the workflow of FIG. 10.
Figure 11B:
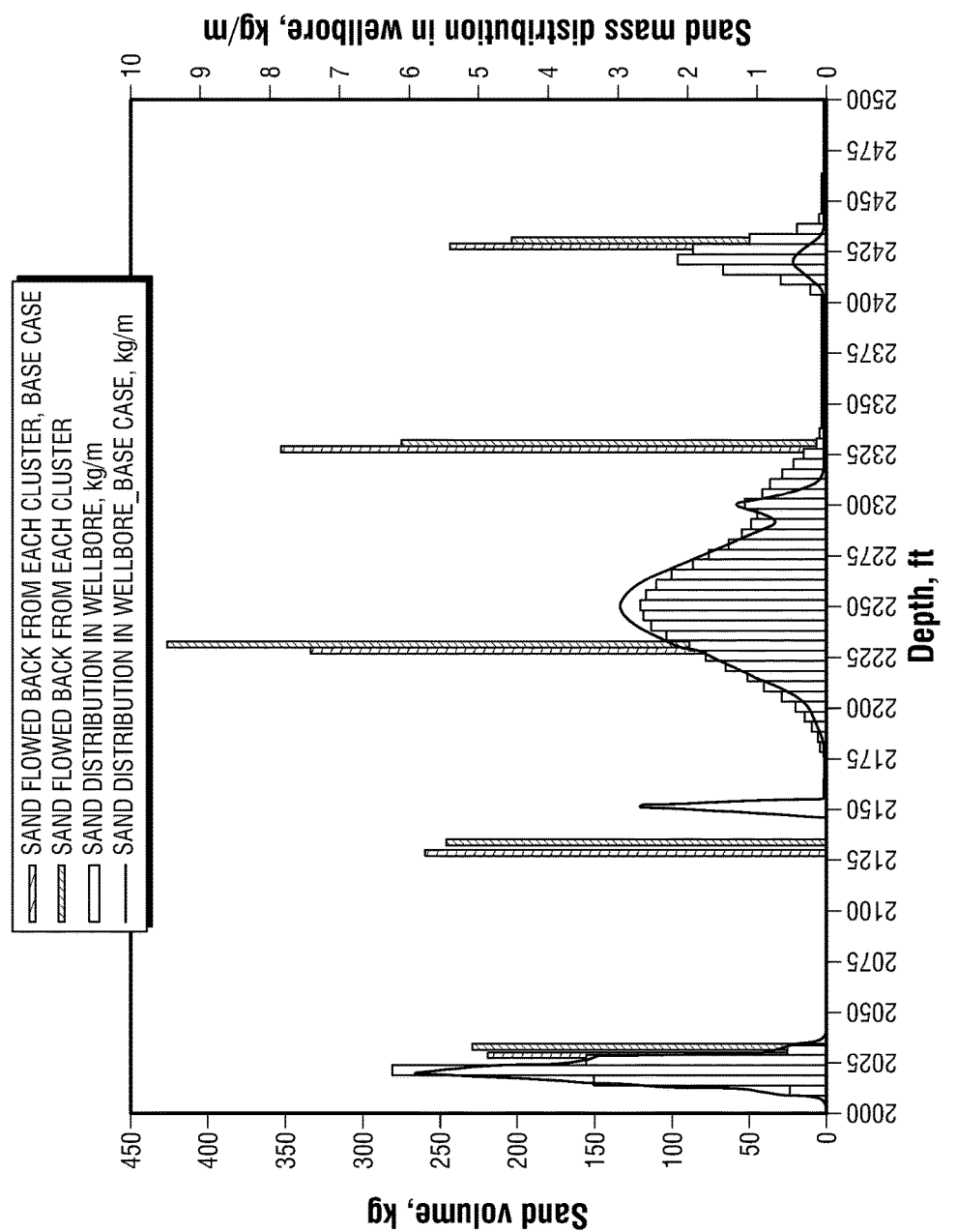

FIGS. 11A and 11B are plots that illustrate the data processing operations of the data analyzer during an exemplary slightly underbalanced clean out operation according to the workflow of FIG. 10. In this example, the clean out operation is performed on a well over a sequence of five perforated zones at depths ranging from 2000-2500 m with a pumping rate of fluid of 0.5 m3/min. The annulus volume capacity of the well was 0.07854 m3/m which corresponds to internal wellbore diameter of 0.112 m and tubing external diameter of 0.0508 m. (model data). The five perforated zones are located at depths of 2030, 2130, 2230, 2330 and 2430 m.

FIG. 11A show a plot of the measured solid concentration as derived in block 1003 as function of BHA location (depth) in the well, which is labeled "measured sand conc." It also shows a plot of the modeled sand concentration as derived in block 1005 as a function of as function of BHA location (depth) in the well, which is labeled "sand concentration." It also shows a plot of total solids volume, labeled "total sand volume."

FIG. 11B shows plots that represent a profile of solids production over the sequence of five perforated zones as derived from the model fitting and calculations of blocks 1007 and 1009. The plots labeled "sand flowed back" represent the volume of solids (in kg) produced from fractures over well depths that encompass the sequence of five perforated zones as derived from the parameters $V_{solids_i}$ of the sequence of perforated zones. And the plots labeled "sand distribution" represent the mass distribution (in kg/m) of deposited solids over well depths that encompass the sequence of five perforated zones as derived by the parameter $\overline{M}_{solid}$ of Eqn. (5).

Note that the parameter(s) that characterize solids production of the intervals and associated perforated zones of the well can be used to dynamically control the operation of the clean out operation. For example, the parameter(s) that characterize the solids produced from fractures can be used to control the pumping rate of the fluid supplied downhole for balanced return where there is little or no solid produced from the fractures during the clean out operation.

In other cases, the return rate can be higher than the pumping rate of the fluid supplied downhole and spikes in the solid concentration in the return fluid can be attributed to both deposited solids from the wellbore and solid production from fractures. The maximum possible solid produce from a perforated zone can be computed as an excess between total local solid production and volumes of sand that can be accumulated in the wellbore. For example, for a wellbore section with length of 10 m and internal diameter of 0.1 m having one perforated zone and produced sand volume of 500 kg, the potential maximum volume of sand with SG of 2.65 and bulk density of 1.6 g/cm3 produced from such perforated interval can be estimated as 500-3.14*(0.1)^2/4/1000*1.6=374 kg. The maximum volume can be used as a constraint whereby measured solid volumes above this limit can be attributed to solids produced from fractures or the formation (and not from deposited sand in the wellbore).

There have been described and illustrated herein several embodiments of a method and system for establishing well performance during plug mill-out and cleanout/workover operations. While particular embodiments have been described, it is not intended that the disclosure be limited thereto, as it is intended that the disclosure be as broad in scope as the art will allow and that the specification be read likewise. In addition, while particular types of devices have been disclosed, it will be understood that other devices having the same function(s) can be used. It will therefore be appreciated by those skilled in the art that yet other modifications could be made to the provided disclosure without deviating from its spirit and scope as claimed.

What is claimed is:

1. A method for characterizing a hydraulically-fractured hydrocarbon-bearing formation that is traversed by a well having a plurality of intervals between a surface and bottom of the well, the method comprising:
analyzing flow characteristics of return fluid that flows from an interval of the plurality of intervals back to a surface-located facility during well operations; and
characterizing at least one local formation property of the hydraulically-fractured formation adjacent to the interval based on the flow characteristics.

2. The method according to claim 1, wherein:
each interval of the plurality of intervals is hydraulically isolated from every other interval of the plurality of intervals by corresponding plugs; and
the interval is a newly-opened well interval that is opened by plug mill-out operations.

3. The method according to claim 2, wherein:
the analyzing of the flow characteristics of the return fluid uses measurements of surface flow characteristics of the return fluid and the downhole pressure measurements to calculate and model return outflow from all open intervals, including the newly-opened interval.

4. The method according to claim 3, wherein:
the analyzing of the flow characteristics of the return fluid calculates the return outflow of the newly-opened interval by isolating the contribution of return outflow for the newly-opened interval from a previous model of return outflow for from all open intervals.

5. The method according to claim 4, wherein:
the contribution of return outflow for the newly-opened interval is derived from incremental changes to a model over successive plug mill-out operations and corresponding intervals.

6. The method according to claim 3, wherein:
the hydrostatic pressure of the milling fluid supplied to the downhole milling bit is greater than formation pressure, and the analyzing of the flow characteristics of the return fluid calculates the outflow of milling fluid into fractures of the newly-opened well interval.

7. The method according to claim 6, wherein:
the at least one local formation property is derived from the calculated outflow of milling fluid into fractures of the newly-opened well interval.

8. The method according to claim 6, wherein:
the milling fluid is water-based, and the analyzing of the flow characteristics of the return fluid analyzes flow characteristics of a water phase at the surface to calculate the outflow of milling fluid into fractures of the newly-opened well interval.

9. The method according to claim 6, wherein:
the milling fluid is oil-based, and the analyzing of the flow characteristics of the return fluid analyzes flow characteristics of an oil phase at the surface to calculate the outflow of milling fluid into fractures of the newly-opened well interval.

10. The method according to claim 3, wherein:
the hydrostatic pressure of the milling fluid supplied to the downhole milling bit is less than formation pressure, and the analyzing of the flow characteristics of the return fluid calculates the inflow of water, oil, gas and/or solids from the fracture and/or formation into the newly-opened interval based on the return outflow for the newly-opened interval.

11. The method according to claim 10, wherein:
the at least one local formation property is derived from the calculated inflow of water, oil, gas, solids, or a combination thereof from the fracture and/or formation into the newly-opened interval.

12. The method according to claim 10, wherein the analyzing of the flow characteristics of the return fluid analyzes flow characteristics of a plurality of different phases at the surface to calculate the inflow of water, oil, gas, solids, or a combination thereof from the fracture and/or formation into the newly-opened interval.

13. The method according to claim 1, wherein:
the interval is subject to a well cleanup or workover operation.

14. The method according to claim 1, wherein:
the at least one local formation property is selected from the group including
fracture area;
fracture conductivity;
fracture connectivity with wellbore;
fracture geometry; formation pressure; formation productivity;
whether or not the interval is in communication with the local region of the formation adjacent to the interval;
the number of fractures (or fracture clusters) in communication with the local region of the formation adjacent to the interval;
whether or not the fractures that were created by hydraulic fracturing of the formation adjacent to the interval provide fluid communication (such as behind-the-casing fluid communication) with the fractures adjacent to a neighboring interval;
whether or not the local region of the formation that is connected to the interval by fractures is normally-pressured, over-pressured or under-pressured (which is an indication of a depleted zone);
whether or not the local region of the formation that is connected to the interval by fractures is overbalanced or underbalanced with respect to the wellbore at the time of the mill-out operations;
whether or not the local region of the formation that is connected to the interval by fractures is prone to either proppant production, formation failure of both;
wettability and propensity to fluid leakoff and imbibition for the local region of the formation that is connected to the interval by fractures;
rock quality of the formation, such as porosity, hydrocarbon content, mineralogy, and formation toughness, lamination density, and density of natural/induced fractures; and
mechanical properties of the formation, such as stress, Young modulus, and Poison ratio.

15. The method according to claim 1, wherein:
the flow characteristics of the return fluid are derived from the output of a surface-located multiphase flow meter.

16. The method according to claim 1, wherein:
the return fluid includes milling fluid that is supplied to a downhole milling bit for milling out a plug.

17. The method according to claim 16, wherein:
hydrostatic pressure of the milling fluid supplied to the downhole milling bit is greater than formation pressure.

18. The method according to claim 17, wherein:
the analyzing of the flow characteristics of the return fluid accounts for an outflow of milling fluid into fractures of the newly-opened well interval.

19. The method according to claim 16, wherein:
hydrostatic pressure of the milling fluid supplied to the downhole milling bit is less than formation pressure.

20. The method according to claim 19, wherein:
the analyzing of the flow characteristics of the return fluid accounts for an inflow of fluid from fractures of the newly-opened well interval.

21. The method according to claim 1, wherein:
the inflow of fluid from fractures of the particular interval includes at least one of: water-based fluid, oil, gas and solids.

22. The method according to claim 1, wherein:
the analyzing of the flow characteristics of the return fluid is based on data gathered under steady-state conditions where there are no surface-controlled variations in well pressure.

23. The method according to claim 1, wherein:
the analyzing of the flow characteristics of the return fluid is based on data gathered under conditions where there are surface-controlled transient variations in well pressure.

24. The method according to claim 1, wherein:
a working fluid is supplied downhole during the well operations, wherein the working fluid incorporates at least one tracer compound to help quantitatively distinguish the working fluid from reservoir fluids.

25. The method according to claim 24, further comprising: using a surface-located chemical analyzer to measure concentration of the at least one tracer compound in return fluid that flows to the surface in order to discriminate between sources and sinks of the working fluid, reservoir fluids, or both during the well operations.

26. The method according to claim 24, further comprising: varying concentration of the tracer compound(s) in a controlled manner in conjunction with controlled pressure variations of the working fluid supplied downhole during the well operations in order to discriminate between sources and sinks of reservoir fluids during the well t operations.

27. The method according to claim 1, wherein:
at least one tracer compound is incorporated into fracturing fluid used to fracture the formation; and
a working fluid is supplied downhole during the well operations;
wherein the at least one tracer compound can help quantitatively distinguish the fracturing fluid from the working fluid, other reservoir fluids (such as connate water), or both.

28. The method according to claim 27, further comprising:
using a surface-located chemical analyzer to concentration of the at least one tracer compound in return fluid that flows to the surface in order to discriminate between sources and sinks of reservoir fluids during the well operations.

29. The method according to claim 1, further comprising:
tagging fluid elements of working fluid that is pumped downhole;
measuring one or more fluid properties of the respective fluid elements that are pumped downhole;
detecting respective tagged fluid elements as part of return fluid at the surface;
measuring one or more fluid properties of the respective fluid elements that are detected as part of return fluid at the surface; and
comparing the fluid properties of the tagged fluid elements from supply to return at the surface in order to characterize the injectivity or inflow from a particular well interval and to characterize the local formation properties of the particular well interval.

30. The method according to claim 29, wherein:
the measuring of the one or more fluid properties of the respective fluid elements that are pumped downhole involves a surface-located gas analysis system that extracts and quantitatively analyzes the concentration of hydrocarbon gas entrained in the respective fluid elements that are pumped downhole; and
the measuring of the one or more fluid properties of the respective fluid elements that are detected as part of return fluid at the surface involves uses a surface-located gas analysis system that extracts and quantitatively analyzes the concentration of hydrocarbon gas entrained in the respective fluid elements that are part of the return fluid at the surface.

31. A method for characterizing a hydraulically-fractured hydrocarbon-bearing formation that is traversed by a well having a plurality of intervals between a surface and a bottom of the well, the method comprising:
- analyzing flow characteristics of return fluid that flows from one or more intervals of the plurality of intervals back to a surface-located facility during well operations; and
- characterizing at least one property relating to solids production of the one or more intervals based on the flow characteristics.

32. The method according to claim 31, wherein:
the surface flow characteristics of the return fluid are measured by a surface-located multiphase flow meter.

33. The method according to claim 31, wherein:
each interval of the plurality of intervals are is hydraulically isolated from every other interval of the plurality of intervals by corresponding plugs; and the one or more intervals are opened by plug mill-out operations.

34. The method according to claim 33, wherein:
the at least one property characterize solids production from fractures that are in fluid communication with a perforated zone of the formation.

35. The method according to claim 34, wherein:
the at least one property further characterizes a profile of solids production from fractures that are in fluid communication with a plurality of perforated zones of the formation.

36. The method according to claim 33, wherein:
the at least one property characterizes deposited solids in the one or more intervals.

37. The method according to claim 36, wherein:
the at least one property further characterizes a profile of deposited solids in the one or more intervals.

* * * * *